(12) United States Patent
Tan et al.

(10) Patent No.: US 7,524,630 B2
(45) Date of Patent: *Apr. 28, 2009

(54) FUNCTIONALIZED NANOPARTICLES AND METHODS OF USE

(75) Inventors: Weihong Tan, Gainesville, FL (US); Jin Shouguang, Gainesville, FL (US); Xiaojun Zhao, Gainesville, FL (US); Rovelyn Tapec Dytioco, Seattle, WA (US); Timothy James Drake, Gainesville, FL (US); Lisa Renee Hilliard, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 841 days.

This patent is subject to a terminal disclaimer.

(21) Appl. No.: 10/421,491

(22) Filed: Apr. 22, 2003

(65) Prior Publication Data

US 2004/0067503 A1 Apr. 8, 2004

Related U.S. Application Data

(60) Provisional application No. 60/375,122, filed on Apr. 22, 2002, provisional application No. 60/374,405, filed on Apr. 22, 2002.

(51) Int. Cl.
*G01N 33/552* (2006.01)
*G01N 33/553* (2006.01)

(52) U.S. Cl. .......................... 435/6; 436/524; 436/525; 436/526; 436/527

(58) Field of Classification Search .............. None
See application file for complete search history.

(56) References Cited

U.S. PATENT DOCUMENTS

| | | | |
|---|---|---|---|
| 4,297,337 A * | 10/1981 | Mansfield et al. | 436/527 |
| 5,091,206 A | 2/1992 | Wang et al. | |
| 5,990,479 A | 11/1999 | Weiss et al. | |
| 6,319,426 B1 | 11/2001 | Bawendi et al. | |
| 6,500,622 B2 * | 12/2002 | Bruchez et al. | 435/6 |
| 6,548,264 B1 * | 4/2003 | Tan et al. | 435/7.21 |
| 6,653,080 B2 * | 11/2003 | Bruchez et al. | 435/6 |
| 6,924,116 B2 | 8/2005 | Tan et al. | |
| 7,129,048 B2 * | 10/2006 | Bruchez et al. | 435/6 |
| 2002/0034747 A1 * | 3/2002 | Bruchez et al. | 435/6 |
| 2002/0039732 A1 * | 4/2002 | Bruchez et al. | 435/6 |
| 2003/0165951 A1 * | 9/2003 | Bruchez et al. | 435/6 |

FOREIGN PATENT DOCUMENTS

EP  0 240 770  10/1987

(Continued)

OTHER PUBLICATIONS

EP 03 72 8505 Search Report dated Jun. 27, 2005.

(Continued)

*Primary Examiner*—Christopher L Chin
(74) *Attorney, Agent, or Firm*—Edwards Angell Palmer & Dodge LLP; Peter F. Corless; Jonathan M. Sparks

(57) ABSTRACT

Silica-coated nanoparticles functionalized with biologically active molecules such as antibodies and nucleotides are used to label cells, to detect and isolate nucleic acid molecules having specific nucleotide sequences, and to separate a mixture of different nucleic acid molecules.

4 Claims, 10 Drawing Sheets

FOREIGN PATENT DOCUMENTS

| | | |
|---|---|---|
| EP | 1 260 595 | 11/2002 |
| WO | WO 98/51435 | 11/1998 |
| WO | WO-01/19405 | 3/2001 |
| WO | WO 01/88540 | 11/2001 |

OTHER PUBLICATIONS

Bonnet et al., "Thermodynamic basis of the enhanced specificity of structured DNA probes," Proc. Natl. Acad. Sci., 96: 6171-6176, May 1999.

Fang et al., "Designing a Novel Molecular Beacon for Surface-Immobilized DNA Hybridization Studies," J. Am. Chem. Soc., 121: 2921-2922, 1999.

Kostrikis et al., "Spectral Genotyping of Human Alleles," Science, vol. 279 (5354), 1998.

Leone et al., "Molecular beacon probes combined with amlification by NASBA enable homogeneous, real-time detection of RNA," Nucleic Acids Research, 26: 2150-2155, 1998.

Sokol et al., "Real time detection of DNA RNA hybridization in living cells," Proc. Natl. Acad. Sci., 95: 11538-11543, 1998.

Tyagi S. and Fred R. Kramer, "Molecular Beacons: Probes that Fluoresce upon Hybridization," Nature Biotechnology, 14: 303-308, 1996.

Tyagi et al., "Multicolor molecular beacons for allele discrimination," Nature Biotechnology, 16: 49-53, 1998.

Vet, et al., "Multiplex detection of four pathogenic retroviruses using molecular beacons," Proc. Natl. Acad. Sci., 96: 6394-6399, 1999.

Giesendorf et al., Molecular beacons: a new approach for semiautomated mutation analysis, Clinical Chemistry 44: 482-486, 1998.

Fang X. and W. Tan, "Imaging Single Flourescent Molecules at the Interfce of an Optical Fiber Probe by Evanescent Wave Excitation," Anal. Chem. 71: 3101-3105, 1999.

Zhang P. and W. Tan, "Direct Observation of Single-Molecule Generation at a Solid-Liquid Interface," Chem. Eur. J., 6: 1087-1092, 2000.

* cited by examiner

SEQUENCE LISTING

<160> NUMBER OF SEQ ID NOS: 19

<210> SEQ ID NO 1

```
<211> LENGTH: 13
<212> TYPE: DNA
<213> ORGANISM: Artificial
<220> FEATURE:
<223> OTHER INFORMATION: Artificially Synthesized Oligonucleotide

<400> SEQUENCE: 1
taacaataat cct                                                        13

<210> SEQ ID NO 2
<211> LENGTH: 16
<212> TYPE: DNA
<213> ORGANISM: Artificial
<220> FEATURE:
<223> OTHER INFORMATION: Artificially Synthesized Oligonucleotide

<400> SEQUENCE: 2
tatccttatc aatatt                                                     16

<210> SEQ ID NO 3
<211> LENGTH: 27
<212> TYPE: DNA
<213> ORGANISM: Artificial
<220> FEATURE:
<223> OTHER INFORMATION: Artificially Synthesized Oligonucleotide

<400> SEQUENCE: 3
ggattattgt taaatttaga taaggat                                         27

<210> SEQ ID NO 4
<211> LENGTH: 27
<212> TYPE: DNA
<213> ORGANISM: Artificial
<220> FEATURE:
<223> OTHER INFORMATION: Artificially Synthesized Oligonucleotide

<400> SEQUENCE: 4
ggataattgt taaatttaga taaggat                                         27

<210> SEQ ID NO 5
<211> LENGTH: 18
<212> TYPE: DNA
<213> ORGANISM: Artificial
<220> FEATURE:
<223> OTHER INFORMATION: Artificially Synthesized Oligonucleotide

<400> SEQUENCE: 5
ttccttcctg ggcatgga                                                   18

<210> SEQ ID NO 6
<211> LENGTH: 28
<212> TYPE: DNA
<213> ORGANISM: Artificial
<220> FEATURE:
<223> OTHER INFORMATION: Artificially Synthesized Oligonucleotide
<220> FEATURE:
<221> NAME/KEY: misc_feature
<222> LOCATION: (26)..(26)
<223> OTHER INFORMATION: Biotin dT

<400> SEQUENCE: 6
gcacgtccat gcccaggaag gaacgtgc                                        28

<210> SEQ ID NO 7
<211> LENGTH: 15
<212> TYPE: DNA
<213> ORGANISM: Artificial
```

```
<220> FEATURE:
<223> OTHER INFORMATION: Artificially Synthesized Oligonucleotide

<400> SEQUENCE: 7
atcaatattt aacaa                                                    15

<210> SEQ ID NO 8
<211> LENGTH: 15
<212> TYPE: DNA
<213> ORGANISM: Artificial
<220> FEATURE:
<223> OTHER INFORMATION: Artificially Synthesized Oligonucleotide

<400> SEQUENCE: 8
ttgttaaata ttgat                                                    15

<210> SEQ ID NO 9
<211> LENGTH: 15
<212> TYPE: DNA
<213> ORGANISM: Artificial
<220> FEATURE:
<223> OTHER INFORMATION: Artificially Synthesized Oligonucleotide

<400> SEQUENCE: 9
ttattaaata ttgat                                                    15

<210> SEQ ID NO 10
<211> LENGTH: 15
<212> TYPE: DNA
<213> ORGANISM: Artificial
<220> FEATURE:
<223> OTHER INFORMATION: Artificially Synthesized Oligonucleotide

<400> SEQUENCE: 10
tagttataaa ttgtt                                                    15

<210> SEQ ID NO 11
<211> LENGTH: 15
<212> TYPE: DNA
<213> ORGANISM: Artificial
<220> FEATURE:
<223> OTHER INFORMATION: Artificially Synthesized Oligonucleotide

<400> SEQUENCE: 11
tagttataaa ttatt                                                    15

<210> SEQ ID NO 12
<211> LENGTH: 28
<212> TYPE: DNA
<213> ORGANISM: Artificial
<220> FEATURE:
<223> OTHER INFORMATION: Artificially Synthesized Oligonucleotide
<220> FEATURE:
<221> NAME/KEY: misc_feature
<222> LOCATION: (1)..(1)
<223> OTHER INFORMATION: carboxy-tetramethyl-rhodamine (TMR)(-C6Am)
<220> FEATURE:
<221> NAME/KEY: misc_feature
<222> LOCATION: (26)..(26)
<223> OTHER INFORMATION: Biotin dT
<220> FEATURE:
<221> NAME/KEY: misc_feature
<222> LOCATION: (28)..(28)
<223> OTHER INFORMATION: DABCYL

<400> SEQUENCE: 12
gcacgtccat gcccaggaag gaacgtgc                                      28
```

```
<210> SEQ ID NO 13
<211> LENGTH: 18
<212> TYPE: DNA
<213> ORGANISM: Artificial
<220> FEATURE:
<223> OTHER INFORMATION: Artificially Synthesized Oligonucleotide

<400> SEQUENCE: 13
ttccttcctg ggcatgga                                                 18

<210> SEQ ID NO 14
<211> LENGTH: 18
<212> TYPE: DNA
<213> ORGANISM: Artificial
<220> FEATURE:
<223> OTHER INFORMATION: Artificially Synthesized Oligonucleotide

<400> SEQUENCE: 14
ttccttcctg ggcatgga                                                 18

<210> SEQ ID NO 15
<211> LENGTH: 16
<212> TYPE: DNA
<213> ORGANISM: Artificial
<220> FEATURE:
<223> OTHER INFORMATION: Artificially Synthesized Oligonucleotide
<220> FEATURE:
<221> NAME/KEY: misc_feature
<222> LOCATION: (1)..(1)
<223> OTHER INFORMATION: Fluorescein

<400> SEQUENCE: 15
catcaatatt taacaa                                                   16

<210> SEQ ID NO 16
<211> LENGTH: 16
<212> TYPE: DNA
<213> ORGANISM: Artificial
<220> FEATURE:
<223> OTHER INFORMATION: Artificially Synthesized Oligonucleotide
<220> FEATURE:
<221> NAME/KEY: misc_feature
<222> LOCATION: (16)..(16)
<223> OTHER INFORMATION: DABCYL

<400> SEQUENCE: 16
ttgttaaata ttgatg                                                   16

<210> SEQ ID NO 17
<211> LENGTH: 16
<212> TYPE: DNA
<213> ORGANISM: Artificial
<220> FEATURE:
<223> OTHER INFORMATION: Artificially Synthesized Oligonucleotide
<220> FEATURE:
<221> NAME/KEY: misc_feature
<222> LOCATION: (16)..(16)
<223> OTHER INFORMATION: DABCYL

<400> SEQUENCE: 17
ttattaaata ttgatg                                                   16

<210> SEQ ID NO 18
<211> LENGTH: 18
<212> TYPE: DNA
<213> ORGANISM: Artificial
<220> FEATURE:
<223> OTHER INFORMATION: Artificially Synthesized Oligonucleotide
```

```
<400> SEQUENCE: 18
gcgcttccgg tgtccaga                                                    18

<210> SEQ ID NO 19
<211> LENGTH: 18
<212> TYPE: DNA
<213> ORGANISM: Artificial
<220> FEATURE:
<223> OTHER INFORMATION: Artificially Synthesized Oligonucleotide

<400> SEQUENCE: 19
gccagggctg tgatctcc                                                    18
```

FUNCTIONALIZED NANOPARTICLES AND METHODS OF USE

CROSS-REFERENCE TO RELATED APPLICATIONS

The present application claims the benefit of U.S. provisional patent application Nos. 60/375,122 and 60/374,405, both of which were filed on Apr. 22, 2002.

STATEMENT AS TO FEDERALLY SPONSORED RESEARCH

This invention was made with U.S. government support under grant number N00014-98-1-0621 awarded by the Office of Naval Research; grant numbers DBI-9871880, CTS-0087676, and CHE-9733650 all awarded by the National Science Foundation; and grant numbers CA92581 and NS39891 both awarded by the National Institutes of Health. The U.S. government may have certain rights in the invention.

FIELD OF THE INVENTION

The invention relates generally to the field of nanoparticles and methods of making and using nanoparticles. More particularly, the invention relates to nanoparticles coated with biologically active substances and methods of using such nanoparticles.

BACKGROUND OF THE INVENTION

Nanoparticles are very small particles typically ranging in size from as small as one nanometer to as large as several hundred nanometers in diameter. Their small size allows nanoparticles to be exploited to produce a variety of products including, for example, tools useful in many different biological and medical applications.

SUMMARY

The invention is based on the development of nanoparticles conjugated to one or more biologically active molecules such as nucleic acids, antibodies, and enzymes. The nanoparticles of the invention can be used as signaling probes and separation tools for ultra-sensitive cell labeling and nucleic acid analysis and separation.

Accordingly, the invention features a method of directing a nanoparticle to a target molecule. The method includes the steps of providing a nanoparticle having a silica surface conjugated with at least one functional group capable of specifically binding the target molecule; and then mixing together the nanoparticle and the target molecule under conditions that allow the at least one functional group to bind the target molecule.

The nanoparticle used can have a core enveloped by the silica surface. The core can be a metal (e.g., a magnetic metal) or a dye (e.g., an organic or inorganic dye). The functional group conjugated to the silica surface can be a protein such as an antibody, an enzyme, avidin, or biotin. It can also be a nucleic acid such as a DNA. The nucleic acid can be in the form of a molecular beacon, e.g., one conjugated with a fluorophore and a quencher of the fluorophore. The functional group can be conjugated to the silica surface via a biotin-avidin linkage.

The target molecule to which the nanoparticle is directed can be one within a cell, one on the cell's surface or in the cell's interior. The cell can be a eukaryotic cell such as a mammalian cell (e.g., a cancer cell), or it can be a prokaryotic cell such as a bacterium. The target molecule can also be one contained in a liquid.

The method of the invention can further include a step of detecting binding of the nanoparticle to the target molecule, e.g., wherein binding of the nanoparticle to the target molecule is detected by observing a change in a property (e.g., light emission) of the nanoparticle. Where the target molecule is contained within a mixture, the method can include a step of isolating from the mixture a complex comprising the nanoparticle bound to the target molecule, a step of separating the target molecule from complex.

As used herein, the word "nanoparticle" means a particle having a diameter of between about 1 and 1000 nm. By reference to the "size" of a nanoparticle is meant the length of the largest straight dimension of the nanoparticle. For example, the size of a perfectly spherical nanoparticle is its diameter.

As used herein, a "nucleic acid" or a "nucleic acid molecule" means a chain of two or more nucleotides such as RNA (ribonucleic acid) and DNA (deoxyribonucleic acid). A "purified" nucleic acid molecule is one that has been substantially separated or isolated away from other nucleic acid sequences in a cell or organism in which the nucleic acid naturally occurs (e.g., 30, 40, 50, 60, 70, 80, 90, 95, 96, 97, 98, 99, 100% free of contaminants).

As used herein, "protein" or "polypeptide" are used synonymously to mean any peptide-linked chain of amino acids, regardless of length or post-translational modification, e.g., glycosylation or phosphorylation.

When referring to hybridization of one nucleic acid to another, "low stringency conditions" means in 10% formamide, 5× Denhart's solution, 6×SSPE, 0.2% SDS at 42° C., followed by washing in 1×SSPE, 0.2% SDS, at 50° C.; "moderate stringency conditions" means in 50% formamide, 5× Denhart's solution, 5×SSPE, 0.2% SDS at 42° C., followed by washing in 0.2×SSPE, 0.2% SDS, at 65° C.; and "high stringency conditions" means in 50% formamide, 5× Denhart's solution, 5×SSPE, 0.2% SDS at 42° C., followed by washing in 0.1×SSPE, and 0.1% SDS at 65° C. The phrase "stringent hybridization conditions" means low, moderate, or high stringency conditions.

As used herein, "sequence identity" means the percentage of identical subunits at corresponding positions in two sequences when the two sequences are aligned to maximize subunit matching, i.e., taking into account gaps and insertions. Sequence identity is present when a subunit position in both of the two sequences is occupied by the same nucleotide or amino acid, e.g., if a given position is occupied by an adenine in each of two DNA molecules, then the molecules are identical at that position. For example, if 7 positions in a sequence 10 nucleotides in length are identical to the corresponding positions in a second 10-nucleotide sequence, then the two sequences have 70% sequence identity. Sequence identity is typically measured using sequence analysis software (e.g., Sequence Analysis Software Package of the Genetics Computer Group, University of Wisconsin Biotechnology Center, 1710 University Avenue, Madison, Wis. 53705).

As used herein, the term "antibody" includes intact polyclonal and monoclonal antibodies as well as antibody fragments.

By the phrase "specifically binds" means that one molecule recognizes and adheres to a particular second molecule in a sample, but does not substantially-recognize or adhere to other molecules in the sample. Generally, a first molecule that "specifically binds" a second molecule is one that binds the second molecule with a binding affinity greater than about $10^5$ to $10^6$ moles per liter.

As used herein, the phrase "functional group" means a chemical group that imparts a particular function to an article (e.g., nanoparticle) bearing the chemical group. For example, functional groups can include biologically active substances such as antibodies, oligonucleotides, biotin, or streptavidin that are known to bind particular molecules; or small chemical groups such as amines, carboxylates, and the like.

By the phrase "conjugated with" is meant covalently or non-covalently bonded to or otherwise stably associated in close proximity to, e.g., by direct or indirect linkage. For example, an avidin-coated nanoparticle can be conjugated with a biotinylated antibody via an avidin-biotin linkage.

Unless otherwise defined, all technical terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions will control. In addition, the particular embodiments discussed below are illustrative only and not intended to be limiting.

DETAILED DESCRIPTION

Biologically active silica-coated nanoparticles are prepared using a water-in-oil microemulsion method that yields uniformly-sized particles composed of a core enveloped by a silica shell. The microemulsion is made by combining a relatively polar liquid such as water, a relatively non-polar liquid such as a liquid alkane, and one or more surfactants to form an isotropic, thermodynamically stable single-phase system. This system is comprised of a plurality of very small spherical water pools (i.e., reverse micelles) that serve as reactors for producing nanoparticle cores. After the cores are produced, they are coated with silica using a silicating agent such as tetraethylorthosilicate (TEOS). To make these silica-coated nanoparticles biologically active, the silica coating is conjugated with one or more biologically active functional groups such as nucleic acids or polypeptides. The below described preferred embodiments illustrate various adaptations of the invention. Nonetheless, from the description of these embodiments, other aspects of the invention can be readily fashioned by making slight adjustments or modifications to the components discussed below.

Nanoparticle Characteristics

Figure 1:
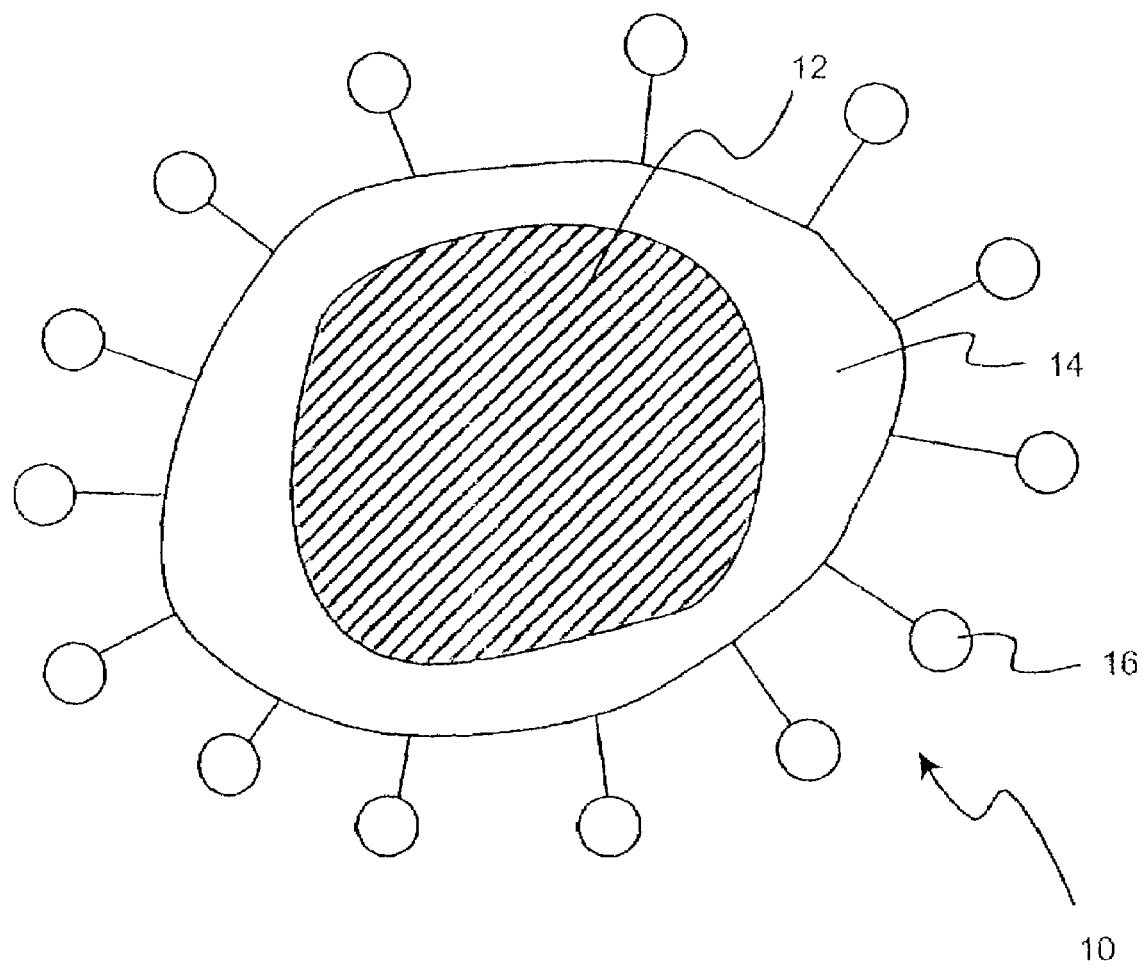
FIG. 1 is a cross-sectional view of a nanoparticle useful in the invention.

In brief overview, referring to FIG. 1, a preferred nanoparticle 10 of the invention includes a core 12, a shell 14 coating core 12, and one or more functional groups 16 derivatized onto shell 14. Although the diameter of nanoparticle 10 can range from about 1 nm to about 1000 nm or larger, for many applications it is preferably between about 10 nm to about 300 nm (e.g., about 10, 15, 20, 25, 30, 35, 50, 75, 100, 150, 200, 250, or 300 nm). In a dispersion of a plurality of nanoparticles 10, the size distribution preferably has a standard deviation of no more than about 25% (e.g., 1, 2, 3, 5, 10, 15, 20, and 25%) of the average diameter (or largest straight dimension) of the plurality of nanoparticles 10.

The nanoparticle 10 illustrated in FIG. 1 is solid (i.e., substantially without pores). While this form is preferred for many applications, nanoparticles within the invention can also be porous. Solid forms can be prepared as described below by uniformly coating core 12 with shell 14. Porous forms can be made by degrading a solid nanoparticle with a corrosive agent (e.g., a very basic solution where shell 14 is composed of silica), and optionally re-coating core 12 with silica. In general, solid forms are preferred when it is desired to sequester core 12 from the outside environment; whereas porous forms are preferred when it is desired to increase the surface area of shell 14 in contact with the outside environment (e.g., where nanoparticle 10 is used a catalyst) or sometimes when nanoparticle 10 is used to isolate various substances (e.g., for "trapping" substances within the pores). Pores in nanoparticle 10 can be of any suitable size less than the diameter of nanoparticle 10. For example, such pores can average about 0.2, 0.5, 1, 2, 3, 5, 10, 20, 50, or 100 nm in size.

Core 12 can be composed of any substance compatible with shell 14. As core 12 imparts functional characteristics on nanoparticle 10, one skilled in the art can select the composition of core 12 to suit the particular application intended for nanoparticle 10 based on known characteristics of compositions. For example, in a preferred embodiment where nanoparticle 10 is desired to be magnetic, core 12 is made up of a magnetic metal such as magnetite ($Fe_3O_4$), maghemite ($\gamma Fe_2O_3$), or greigite ($Fe_3S_4$). In this example, the composition of core 12 imparts a magnetic quality on nanoparticle 10 such that nanoparticle 10 can be used for magnetically based applications, e.g., cell separation/purification.

For other applications, core 12 can be made up of non-magnetic metals or metal salts (e.g., gold, silver, cadmium sulfide, etc.). For example, nanoparticles having CdS cores coated with silica can be used as highly flourescent or luminescent probes. As another example, for the production of dye or pigment nanoparticles, core 12 can include inorganic salts useful in preparing "pigmentless" pigments, e.g., europium salts, tris(2,2'-bipyridyl) dichlororuthenium (Ru/Bpy), potassium permanganate, potassium dichromate, nickel sulfate, cobalt chloride, iron(III) chloride, copper nitrate, etc.

Core 12 may also be composed of a fluorescent or luminescent organic dye. Many such organic dyes are known. See, e.g., *Handbook of Fluorescent Probes and Research Products*, 8th Edition, Molecular Probes Inc. Specific examples of useful dyes include rhodamine 6G (R6G), carboxy-tetramethyl-rhodamine (TMR), and fluorescein. In photostability experiments, the intensity of pure R6G was shown to decrease rapidly, while the fluorescence intensity of the same R6G inside a nanoparticle was not changed significantly under the same conditions. The improved photostability of such dye-doped nanoparticles minimizes photobleaching and improves the accuracy of assays that utilize such fluorophores. Core 12 can also be composed of a mixture of different substances. For example, where it is desired to make a magnetic, dye-doped nanoparticle, core 12 can be composed of both a magnetic metal and a dye.

Core 12 can be of any size less than the size of nanoparticle 10. Thus, core 12 can have a diameter of between less than 1 and 1000 nm. For many applications, core 12 preferably has a diameter ranging from about 1 to about 200 nm. As one example, because animals are able to excrete nanoparticles sized less than about 100 nm, but retain particles greater than 100 nm (primarily in the liver and spleen), cores small enough to be incorporated in nanoparticles less than 100 nm in size are preferred in diagnostic or therapeutic applications where is it desired that the nanoparticles not be retained in a subject.

When made using a microemulsion nanoparticle-manufacturing technique (see below), core 12 generally has a spheroid shape (conventional reverse micelles are spheroid). Core 12, however, is not limited to a spheroid shape. For example, rather than being perfectly round, nanoparticle 10 can be oblong or tube-like, a shape preferred in many magnetic applications. Where core 12 is in crystalline form, nanoparticle 10 can have a regular or irregular polyhedral shape such as a cuboid shape.

Shell 14 is a substance that coats core 12. It can be composed of any compatible material that can be coated onto core 12 using the methods of the invention. Shell 14 can, for example, be composed of a polymer (e.g., polystyrene, polyethylene, polyvinyl chloride, an acrylic polymer, etc.), a polysaccharide such as dextran, an inorganic oxide such as alumina or silica, or mixtures of the foregoing. In the presently preferred embodiment, shell 14 is composed partially or entirely of silica. Silica is preferred in various applications as it is relatively inert in many environments, is biocompatible, prevents agglomeration with other nanoparticles in a dispersion, and can be readily derivatized with many different functional groups. And while FIG. 1 shows shell 14 configured in a single layer, it can also be multi-layered. For example, shell 14 can include a first layer of silica coating and immediately adjacent to core 12, and a second layer coating the silica layer. The second layer can be composed of any substance that can be coated onto the first layer. For example, the second layer can be composed of a biodegradable material (e.g., a sugar or polymer) impregnated with a drug. When introduced to an animal, the biodegradable material and drug will gradually be dissolved into the animal. In other applications, shell 14 can be composed of 3, 4, 5 or more separate layers.

In the preferred embodiment shown in FIG. 1, shell 14 is shown completely enveloping core 12 and thus sequestering core 12 from the outside environment. This form is preferred where it is desired to prevent interaction of core 12 with external factors. For example, a silica coating can prevent corrosion of an iron-based core. Similarly, a complete silica coating can enhance the shelf life of a nanoparticle-based pigment by preventing degradation or dissolution of the pigment in a solvent or by oxidation. In some variations, nanoparticle 10 does not include a shell 14 or is only partially coated with a shell 14 (e.g., where shell 14 has been partially dissolved or degraded off core 12).

Shell 14 can be of any thickness (i.e., length from outside surface of core 12 to outside surface of shell 14) compatible with the methods of making nanoparticle 10. Using preferred methods of the invention, shell 14 can be made to have a thickness ranging from less than about 1 nm to greater than about 300 nm. Depending on the particular application that nanoparticle 10 is to be used in, the preferred thicknesses of shell 14 will vary. For example, a relatively thick shell is generally preferred where it is desired to reduce agglomeration of nanoparticles (where the cores attract one another) or degradation of the shell (e.g., in a caustic solvent). On the other hand, where it is desired to amplify the properties of the core (e.g., color of a pigment), a relatively thinner shell is generally preferred.

As shown in FIG. 1, functional groups 16 can be derivatized onto the surface of shell 14. Functional groups 16 can take the form of any chemical or biological group that can be attached to nanoparticle 10 via shell 14. For example, functional groups 16 can be a biologically active substance, e.g., proteins such as antibodies (monoclonal, polyclonal), enzymes, biotin, and streptavidin; nucleic acid molecules (e.g., RNA, DNA); and biochemical groups such as amines and carboxylates.

Methods of Making Nanoparticles

Figure 2:
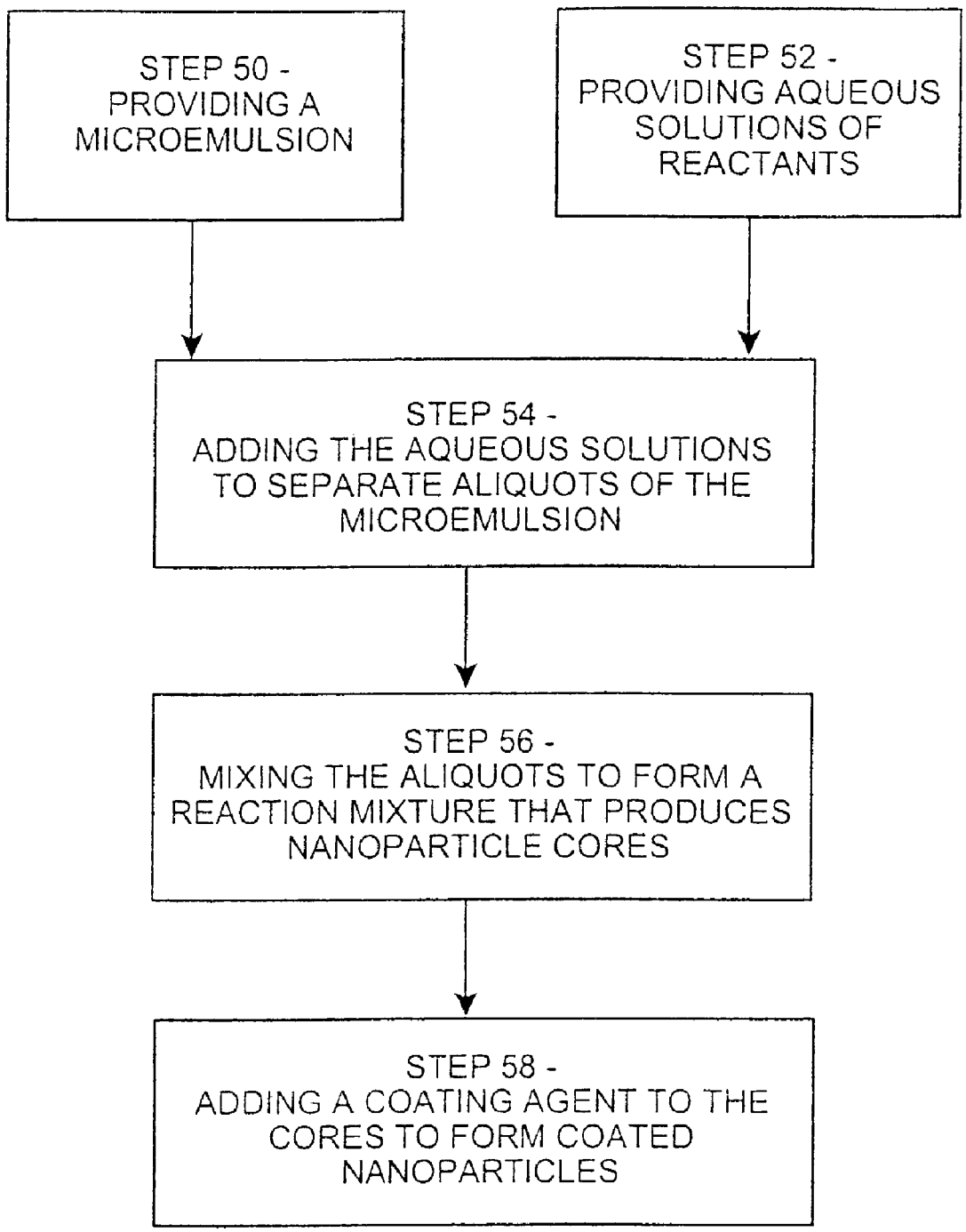
FIG. 2 is a flowchart illustrating general steps involved in a method of making nanoparticles useful the invention.

Referring now to FIG. 2, a preferred method of making nanoparticles includes: a step 50 of providing a microemulsion; a step 52 of providing aqueous solutions of reactants; a step 54 of adding the aqueous solutions to separate aliquots of the microemulsion; a step 56 of mixing the aliquots to form a reaction mixture that produces nanoparticle cores; and a step 58 of adding a coating agent to the cores to form coated nanoparticles.

The microemulsion of step 50 can be made by mixing together at least two immiscible liquids in the presence of at least one surfactant to form a thermodynamically stable, optically isotropic dispersion of nanosize droplets of one or both liquids in the other. The dispersion is stabilized by the surfactant reducing the surface tension at the interface of the two liquids. Microemulsions can be either water-in-oil (i.e., reverse micelles or water droplets dispersed in oil), oil-in-water (i.e., micelles or oil droplets dispersed in water), or a bi-continuous system containing comparable amounts of two immiscible fluids. In some cases, microemulsions can be made by mixing together two non-aqueous liquids of differing polarity with negligible mutual solubility. For use in the invention, water-in-oil microemulsions are presently preferred because they are compatible with very many known chemical reactions for precipitating solids in aqueous solutions.

The immiscible liquids that can be used in step 50 typically include a relatively polar (i.e., hydrophobic) liquid and a relatively non-polar (i.e., hydrophilic) liquid. While a large variety of polar/nonpolar liquid mixtures can be used to form a microemulsion useful in the invention, the choice of particular liquids utilized will depend on the type of nanoparticles being made. A skilled artisan can select specific liquids for particular applications by adapting known methods of making microemulsions for use in the present invention. The presently preferred relatively polar liquid is water, although other polar liquids might also be useful. Water is preferred because it is inexpensive, readily available, non-toxic, easy to handle and store, compatible with a large number of different precipitation reactions, and immiscible in a large number of nonpolar solvents. Examples of suitable non-polar liquids include alkanes (e.g., any liquid form of hexane, heptane, octane, nonane, decane, undecane, dodecane, etc.), cycloalkanes (e.g., cyclopentane, cyclohexane, etc.), aromatic hydrocarbons (e.g., benzene, toluene, etc.), and mixtures of the foregoing (e.g., petroleum and petroleum derivatives). In general, any such non-polar liquid can be used as long as it is compatible with the other components used to form the microemulsion and does not interfere with the involved precipitation reaction.

Step 50 requires at least one surfactant to form a microemulsion. Surfactants are surface active agents that thermodynamically stabilize the very small dispersed micelles or reverse micelles in microemulsions. Typically, surfactants possess an amphipathic structure that allows them to form films with very low interfacial tension between the oily and aqueous phases. Thus, any substance that reduces surface tension at the interface of the relatively polar and relatively non-polar liquids and is compatible with other aspects of the invention can be used to form the microemulsion used to make nanoparticles. The choice of a surfactant will depend on the particular liquids utilized and on the type of nanoparticles being made. Specific surfactants suitable for particular applications can be selected from known methods of making microemulsions or known characteristics of surfactants. For example, non-ionic surfactants are generally preferred when an ionic reactant is used in the microemulsion process and an ionic detergent would bind to or otherwise interfere with the ionic reactant.

Numerous suitable surfactants are known. A nonexhaustive list includes soaps such as potassium oleate, sodium oleate, etc.; anionic detergents such as Aerosol® OT, sodium cholate, sodium caprylate, etc.; cationic detergents such as cetylpyridynium chloride, alkyltrimethylammonium bromides, benzalkonium chloride, cetyldimethylethylammonium bromide, etc; zwitterionic detergents such as N-alkyl-N,N-dimethylammonio-1-propanesulfonates and CHAPS; and non-ionic detergents such as polyoxyethylene esters, polyoxyethylene ethers, polyoxyethylenesorbitan esters, sorbitan esters, and various tritons (e.g., (TX-100, TX-114, etc.).

The concentration of surfactant used in step 50 will depend on many factors including the particular surfactant selected, liquids used, and the type of nanoparticles to be made. Suitable concentrations can be determined empirically, i.e., by trying different concentrations of surfactant until the concentration that performs best in a particular application is found. Ranges of suitable concentrations can also be determined from known critical micelle concentrations.

In preferred embodiments bis (2-ethylhexyl) sulfosuccinate sodium salt (Aerosol® OT, AOT) is used to create a microemulsion of water and isooctane; cetyltrimethylammnonium bromide (CTAB) is used to create a microemulsion of n-hexane, n-hexanol, and water; and triton X-100 (TX-100) is used to make a microemulsion of cyclohexane, n-hexanol, and water. Although, in most applications the invention, step 50 employs only one surfactant to stabilize the microemulsion, one or more cosurfactants can also be used. The use of a cosurfactant is sometimes advantageous for stabilizing reverse micelle systems. For example, adding an aqueous surfactant such as soap to a mixture of oil and water yields a milky emulsification. Adding a co-surfactant such as an alcohol of intermediate chain length causes the milky emulsion to clear spontaneously due to formation of very small spheres of dispersed water droplets in oil. Such cosurfactants function by further reducing the interfacial tension between the phases to facilitate the formation of very small particles of dispersed phase. Suitable co-surfactants for use in the invention include hexanol, butanol, pentanol, octanol, and like intermediate chain length alcohols. The microemulsion of step 50 is prepared by simply mixing together a relatively polar liquid, a relatively non-polar liquid, and one or more surfactants. For preparing a water-in-oil microemulsion (having aqueous reverse micelles), the volume of the relatively non-polar liquid vastly exceeds that of the relatively polar liquid (e.g., non-polar liquid:polar liquid volume ratio between about 10000:1 to 100:1). While addition of the surfactant can sometimes cause a microemulsion to form without further agitation, generally the mixture is mechanically (e.g., magnetically) stirred or ultrasonicated to form the microemulsion. Many microemulsions useful in the invention can be prepared at room temperature (i.e., about 20° C.) without addition of heat. In other cases, to hasten microemulsion formation by increasing the solubility of the surfactant in the liquids, the mixture of ingredients is sometimes heated (e.g., using a hot plate) to between about 25-80° C.

Referring again to FIG. 2, step 52 of providing aqueous solutions of reactants and step 54 of adding the aqueous solutions of step 52 to separate aliquots of a microemulsion can be performed using a water-in-oil microemulsion prepared as described above. Steps 52 and 54 can be accomplished by first providing a first water-soluble reactant (reactant A) and a second water-soluble reactant (reactant B), and then adding reactant A to a first aliquot of a water-in-oil microemulsion and reactant B to a second aliquot of a water-in-oil microemulsion. The two aliquots are separately mixed until reactant A reaches equilibrium distribution in each reverse micelle (reverse micelles continuously form, coalesce, and break apart in the microemulsion, thereby allowing any reactant contained therein to be distributed equally among the reverse micelles) of the first aliquot, and reactant B reaches equilibrium distribution in each reverse micelle of the first aliquot. In step 56, after allowing for the distribution of the dissolved species to equilibrate, the two aliquots are mixed together. Due to collision and coalescence of the reverse micelles, the cations of reactant A and anions of reactant B contact each other and react to form precipitates that serve as nanoparticle cores.

Reactants A and B are generally selected so that they can react to form a precipitate within the reverse micelles of the microemulsions. They are typically soluble in the aqueous reverse micelles and may be solids, liquids, or gases. In a preferred embodiment, Reactant A is a salt (e.g., with the hypothetical formula $A^+X^-$) that dissolves into soluble cations (e.g., $A^+$'s) within the reverse micelles of the first aliquot of the microemulsion, and Reactant B is another salt (e.g., with the hypothetical formula $B^+Y^-$) that dissolves into soluble anions (e.g., $Y^-$'s) within the reverse micelles of the second aliquot of the microemulsion. The cations of Reactant A and anions of Reactant B are selected so that they form a precipitate ($A^+Y^-$) when mixed together in an aqueous solution. While the foregoing illustrates a preferred method of the invention, other methods for making nanoparticle cores using microemulsions are also within the invention. Many of these can be performed by making slight modifications to the preferred method just described. For example, rather than mixing together two different aliquots of a microemulsion, the core-forming reaction can be carried out using a single aliquot of a microemulsion. In this case, a reactant can be added to the single aliquot and allowed to dissolve and equilibrate among the reverse micelles of the microemulsion. Subsequently, a precipitating (e.g., reducing or oxidizing) agent in the form of a liquid or gas (e.g., hydrogen, hydrazine, $NH_4OH$) is added to the single aliquot to precipitate the reactant dissolved in the reverse micelles.

Nanoparticle cores can be isolated from a microemulsion by adding a solvent such as acetone or ethanol to the microemulsion and then filtering and/or centrifuging the mixture to isolate the nanoparticles. For filtering, filters have pores sized smaller than the nanoparticles. For centrifuging, the mixture can be spun at 10,000 RPM or more in a microcentrifuge for 15 minutes or more to pellet the nanoparticles and the supernatant can be decanted. Nanoparticles isolated in this manner can be washed one or more times with acetone or an ethanol/water solution to remove any surfactant or other microemulsion component. The isolated and washed nanoparticles can be dried over acetone. Prior to use or functionalization, the nanoparticles can be resuspended in an appropriate liquid.

Using the water-in-oil microemulsion technique, nanoparticle core size is highly controllable. Although core size generally relates to reverse micelle size, this is not necessarily a strict relationship as core size does not always correlate with the amount of reactant(s) originally present in each reverse micelle. For example, even small nanoparticle cores (e.g., having diameters of 2 nm to 5 nm) contain from about 300 to 1000 atoms, which is in most cases appreciably larger than the number of reactant molecules present in each micelle prior to reaction. This indicates that nanoparticle core nuclei first form in a small fraction of micelles; these then consume the reactant(s) in other micelles through collision-coalescence processes.

A factor to consider in nanoparticle core preparation therefore is the rate at which nanoparticle cores form. The rate at which nanoparticle cores form directly relates to the rate at which the reverse micelles coalesce. Thus, the specific surfactant selected strongly influences the core formation rate, controlling the rate of reverse micelle coalescence. That is, surfactants that result in a relatively rigid interface between the two immiscible liquids of the microemulsion decrease the core formation rate, while surfactants that result in a fluid interface increase the rate. Other properties of the microemulsion, such as ionic strength, pH, and temperature can also be manipulated to control the rate of core formation.

Through empirical adjustment of initial reactant concentrations and microemulsion compositional parameters, nanoparticle cores with homogeneous size distribution (e.g., percentage standard deviation in core size is between about 1 and 5% (for instance, 1, 2, 3, 4, and 5%)) and average diameters ranging from about 1 nm to about 300 nm or more. Cores of larger size (e.g., about 1 micron) can be prepared by: (i) adding a higher concentration of reagent(s) to the reaction medium (e.g., reverse micelles of the microemulsion), and/or (ii) sonochemically (i.e., by ultrasonication) dispersing isolated cores in a suitable solvent other than microemulsion to make a uniform core suspension, and then adding additional reagent to the dispersion. In the latter method, individual cores often fuse.

In most cases, nanoparticle cores made according to the water-in-oil microemulsion technique described above have a spheroid shape (conventional reverse micelles are spheroid). By altering various parameters in the core formation process, it is possible to produce cores having other shapes. For example, oblong or tube-shaped cores can be made by adding a very high concentration of sodium dodecyl sulfate to the microemulsion. As another example, where reactants are selected such that the formed cores have a crystalline structure, nanoparticle cores having a regular or irregular polyhedral shape can be made.

Magnetic nanoparticles can be made using magnetic materials such as magnetite, maghemite, and greigite as part of the core. By varying the overall size and shape of such magnetic cores, they can be made superparamagnetic or stable single-domain (particles that retain a stable magnetic moment after being removed from a magnetic field). Core size relates to whether a magnetic nanoparticle is superparamagnetic or single-domain. Thus, relatively equidimensional superparamagnetic particles generally have a core sized less than 50 to 80 nm. At particle sizes above this upper range, the magnetization of the particle is split into domains of differing magnetization vectors in order to minimize internal magnetic energies. Referring once again to FIG. 2, methods of making nanoparticles within the invention feature a step 58 of adding a coating agent to form coated nanoparticles. The coating agent used in step 58 can be any that causes silica (or another substance) to be deposited onto the surface of the nanoparticle cores. Presently preferred reagents include reactive silicates such as tetraethylorthosilicate (TEOS) or aminopropyltrimethoxysilane (APTS) (both available from Sigma, St. Louis). To coat cores, such reactive silicates are simply added to a solution of nanoparticle cores (e.g., the microemulsion in which the cores were prepared) along with a reducing agent such as ammonium hydroxide or NaOH. The mixture can be stirred for a suitable amount of time to allow the cores to become coated with silica.

Thickness of the silica coating, and the reaction rate for the formation of silica coating are dependent on the amount of reactive silicate added, reaction time, amount of reducing agent added, and reverse micelle size (where coating is performed in a water-in-oil microemulsion). Increasing the concentration of the reducing agent (e.g, [$NH_4OH$]) to reactive silicate concentration (e.g., [TEOS]) generally results in a thicker coating forming after a given reaction time. Increasing the concentration of polar liquid (e.g., water) to reactive silicate concentration generally results in a thinner coating forming after a given reaction time. The precise reaction conditions for controlling the thickness of the coating will vary according to the particular agent used, the core material, etc. These, however, can be determined empirically by simple experiments varying the concentrations of reagents and reaction times and conditions.

Methods within the invention can also include a step of functionalizing (i.e., derivatizing with one or more functional chemical groups) coated nanoparticles made as described above. Numerous known methods for attaching functional groups to silica can be adapted for use in the present invention. (See, e.g., Iler, R., The Chemistry of Silica: Solubility, Polymerization, Colloid and Surface Properties, and Biochemistry, Wiley-Interscience, NY, 1979; VanDerVoort, P. and Vansant, E., Journal of Liquid Chromatography and Related Technologies,19:2723-2752, 1996; Weetall, H. ed., Immobilized Enzymes, Antigens, Antibodies, and Peptides: Preparation and Characterization, M. Dekker, NY, 1975) A typical process for adding functional groups to silica-coated nanoparticles involves treating the nanoparticles with a silanizing agent that reacts with and couples a chemical group to the silica surface of the nanoparticles. The chemical group can itself be the functional group, or it can serve as a substrate to which functional groups can be coupled.

For example, in an exemplary method, silica-coated nanoparticles are prepared as described above and the particle surfaces are silanized using trimethylsilylpropyl-diethylenetriamine (DETA), a silanization agent that attaches primary amine groups to silica surfaces. Antibodies or other proteins can then be covalently coupled to the silanized surface using the cyanogen bromide (CNBR) method. As one example, CNBR-mediated coupling can be achieved by suspending silica-coated nanoparticles previously silanized with DETA in a 2 M sodium carbonate buffer and ultrasonicating the mixture to create a particle suspension. A solution of CNBR (e.g., 2 g CNBR/1 ml acetonitirile) is then added to the particle suspension to activate the nanoparticles. After washing the nanoparticles with a neutral buffer (e.g., PBS, pH 8), an antibody solution is added to the activated nanoparticle suspension causing the antibodies to become bound to the nanoparticles. A glycine solution can also be added to the antibody-coated nanoparticles to block any remaining unreacted sites.

In other methods, a biotin-streptavidin linkage is used to functionalize the nanoparticles. For example, the silica shell of the nanoparticles is first coated with streptavidin using gluteraldehyde-crosslinking to stabilize the avidin on the silica surface. The functional group (e.g., antibody or nucleic acid molecule) is then biotinylated via conventional methods. The biotinylated functional group is then mixed with the avidin-coated nanoparticles to form functional group-coated nanoparticles.

Methods of Using Nanoparticles

The nanoparticles of the invention can be used in a variety of applications. For example, antibody-coated fluorescent nanoparticles can be used to specifically label cells. Nucleic acid-coated fluorescent nanoparticles can be used to detect specific polynucleotides. In addition, nucleic acid-coated magnetic nanoparticles can be used to separate and collect specific polynucleotides, including DNA and RNA from a mixture.

Labeling Cells

Figure 3B:
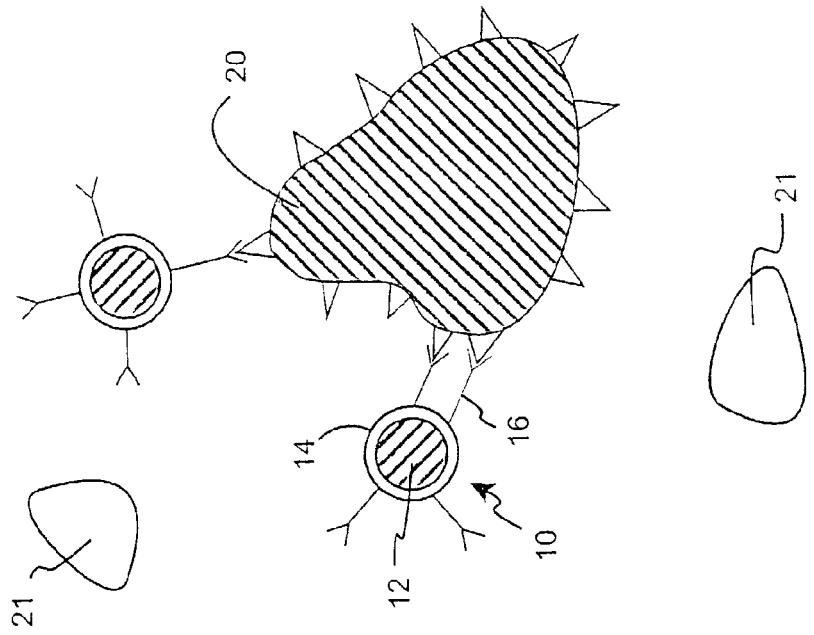
FIG. 3 is two schematic views (A and B) illustrating a method of labeling cells using nanoparticles.
Figure 3A:
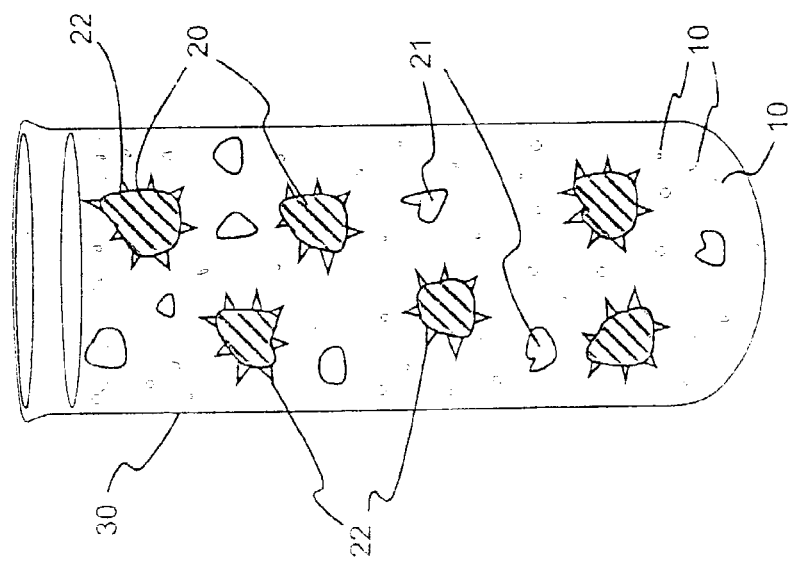

Nanoparticles of the invention can be used to label cells (e.g., eukaryotic or prokaryotic cells). One such method is illustrated in FIG. 3. Referring to FIG. 3A, antibody-derivatized dye-doped nanoparticles 10 are shown mixed with target cells 20 (e.g., cancer cells, mammalian cells, human cells, bacterial cells, and the like) and non-target cells 21 in container 30. Target cells 20 express a target antigen 22 on their surface, while non-target cells 21 do not. In the nanoparticles shown, core 12 includes a fluorescent/luminescent material such as R6G, fluorescein, Ru/Bpy or TMR and functional groups 16 include an antibody that can specifically bind target antigen 22. Referring now to FIG. 3B, nanoparticle 10 is shown physically binding target cell 20 via the interaction of functional groups 16 and target antigen 22. Such binding spontaneously results when nanoparticle 10 and target cell 20 are mixed together in container 30 under conditions which allow antibody-antigen binding (e.g., about room temperature, neutral to slightly basic pH in a low salt buffer). Non-target cells 21 do not specifically bind nanoparticles 10 because they do not express target antigen 22.

Nucleic Acid Detection

The invention also provides methods for detecting the presence of a specific target nucleic acid molecule in a sample. One such method utilizes luminescent or fluorescent nanoparticles conjugated with a functional group (e.g., an oligonucleotide that is the complement of a portion or all of the target nucleic acid) that hybridizes to the particular nucleotide sequence of the specific target nucleic acid molecule under given reaction conditions (e.g., stringent hybridization conditions). In this method, the luminescent/fluorescent nanoparticles are added to a sample containing the target nucleic acid molecule having the particular nucleotide sequence, and binding between the nanoparticle and the target nucleic acid molecule having the particular nucleotide sequence is detected, e.g., by analyzing luminescence or fluorescence.

Figure 4:
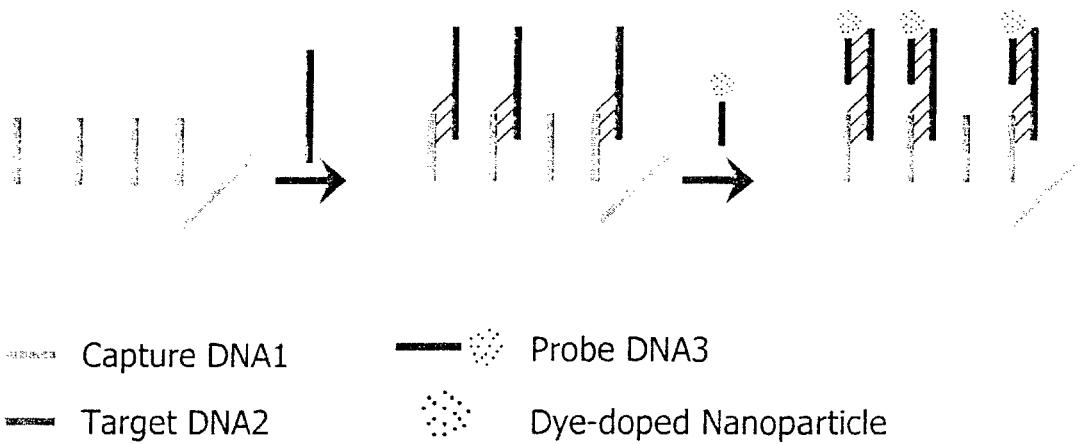
FIG. 4 is a schematic illustration of a method of detecting the presence of a nucleic acid molecule.

Referring to FIG. 4, another method of detecting the presence of a nucleic acid molecule in a sample utilizes nucleic acid molecules immobilized on a substrate. In this method, a capture nucleic acid molecule is immobilized on a suitable substrate such as a silica-coated quartz surface. The sample is then added to the substrate such that if it contains a target nucleic acid molecule having a nucleotide sequence that hybridizes to the capture nucleic acid, the target nucleic acid will bind the capture nucleic acid. To detect this interaction, the substrate is contacted with a probe nucleic acid molecule conjugated to a luminescent or fluorescent nanoparticle. The probe nucleic acid molecule has a nucleotide sequence that hybridizes to the target nucleic acid but not the capture nucleic acid. If the target nucleic acid is present in the sample, an increase in fluorescence/luminescence will be detected on the substrate (e.g., by spectroscopy).

Nucleic Acid Detection Using MBs

Another method of detecting the presence of a nucleic acid and/or separating the nucleic acid from a mixture of nucleic acids utilizes an MB immobilized on a substrate such as a glass plate or a nanoparticle. MBs are single-stranded oligonucleotide probes designed such that in the absence of their target DNA sequences, these molecules possess a stem-and-loop structure (Tyagi S and Kramer F R, Nature Biotechnology,14, 303-308, 1996). The loop portion of the molecule is designed to hybridize with a specific complementary target nucleic acid. The bases at the two ends of the beacon, forming the stem, are complementary to each other. One end of the stem is conjugated to a fluorophore and the other end is conjugated to a quencher. In the absence of the target DNA, the hairpin shape of the molecule brings the fluorophore and the quencher in close proximity. In this configuration, light energy captured by the fluorophore is transferred to the quencher. The quencher is preferably a non-fluorescent chromophore that dissipates the energy it receives from the fluorophore as heat, with the result that the fluorescence intensity of the probe in the hairpin configuration is much less than when the probe is in an open or linear configuration.

Figure 5:
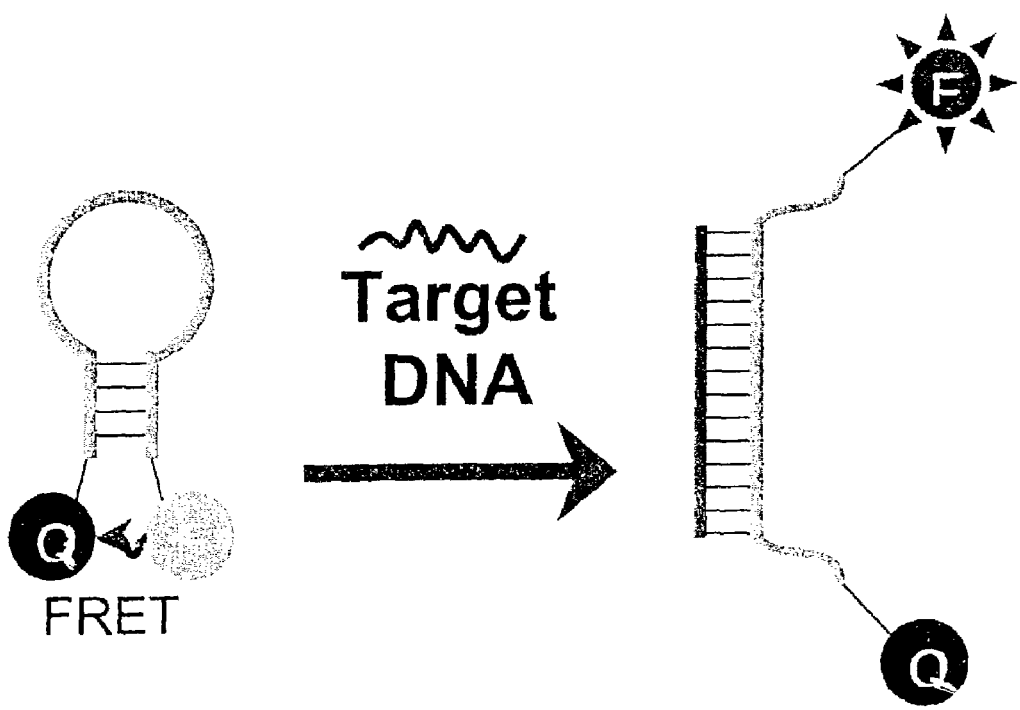
FIG. 5 is a highly schematic illustration of the use of a molecular beacon (MB) for specifically binding and detecting a target nucleic acid molecule having a particular nucleotide sequence.

A MB labeled with a fluorophore and a quencher on the two ends of the stem is shown schematically in FIG. 5. When the probe encounters an appropriate target DNA molecule, its loop portion forms a hybrid that is longer and more stable than the stem. Due to the rigidity and length of the hybrid formed with the target DNA sequence, the continued existence of the stem hybrid is not possible. Thus, upon hybridization with its target DNA sequence, the MB undergoes a spontaneous conformational reorganization that forces the stem apart, and causes the fluorophore and the quencher to move apart. Separation of the fluorophore from the quencher then reverses quenching and allows detection of the fluorescence emitted by the fluorophore. Therefore, MBs emit a more intense fluorescent signal when hybridized to their target molecules then when not. MBs have been successfully used for DNA hybridization studies (Tyagi S and Kramer F R, Nature Biotechnology,14, 303-308, 1996; Tyagi S, Bratu D, Kramer F R , Nature Biotechnology, 16, 49-53, 1998; Kostrikis L G, Tyagi S, Mhlanga M M, Ho D D, Kramer F R, Science 279, 1228-

1229, 1998; Giesendorf B A J, Vet J A M, Tyagi S, Mensink E J M G, Trijbels F J M, Blom H J, Clinical Chemistry ; 44: 482-486, 1998). The size of the loop and its content can be varied by designing different MBs. Also, the quencher and the fluorophores can be varied according to the particular application.

Referring to FIG. 5, the invention provides a MB immobilized on a substrate, such as a solid plate or a nanoparticle, for specifically binding a target nucleic acid molecule having a particular nucleotide sequence. As illustrated in FIG. 5, a preferred MB for use in this method includes a probe oligonucleotide (shown in stem-loop configuration). The oligonucleotide has a nucleotide sequence capable of hybridizing to a target nucleic acid molecule. It is also conjugated to both a fluorophore (e.g., fluorescein or rhodamine-based dyes) and a quencher of the fluorophore (e.g., DABCYL). Any suitable fluorophore-quencher combination may be used, e.g., TMR and DABCYL (see examples section below), so long as fluorescence energy resonance transfer (FRET) occurs when the fluorophore is proximal to the quencher, such that a change in the emission spectra of the fluorophore is detectable. DABCYL [4-(4'-dimethylaminophenylazo benzoic acid)], a non-fluorescent chromophore, is preferred for many applications as it serves as a universal quencher for any fluorophore in MBs (Tyagi S, Bratu D, Kramer F R, Nature Biotechnology, 16, 49-53, 1998).

In the model shown in FIG. 5, the fluorophore is conjugated to one end of the probe oligonucleotide (e.g., the 5' end) and the quencher is conjugated to the opposite end of the oligonucleotide (e.g., the 3' end). In the absence of the target nucleic acid molecule, the probe oligonucleotide is configured in a stem-loop structure (due to self-hybridization) wherein the fluorophore is adjacent to the quencher—a conformation in which FRET causes reduced fluorescence emission from the fluorophore. Methods of designing oligonucleotides that can form such stem-loop structures are well known. When the target nucleic acid molecule is present, it hybridizes to the probe causing the probe to reconfigure into a linear conformation wherein the fluorescence emission increases due to the reduction or elimination of FRET that occurs when the fluorophore and quencher are separated. Thus, presence of the target nucleic acid is determined by observing an increase in fluorescence.

Immobilization of MBs

MBs can be immobilized onto a substrate such as a nanoparticle or slide by adapting known chemical methods. For example, biomolecules can be immobilized onto a solid surface using a biotin-avidin system (Anzai, J., Hoshi, T. and Osa, T. Trends in Analytical Chemistry, 13, 205-210, 1994; Narasaiah, D., Nowall, W. B. and Kuhr, W. G. Anal. Chem.69, 2619-2625, 1997). For instance, in one embodiment of the invention, a biotin molecule is incorporated within the structure of an MB. The biotinylated MB can then be attached to an avidin-coated surface via a biotin-avidin linkage.

Attachment of the biotin functional group to the MB requires positioning of the attachment site to permit optimal hybridization of a target DNA molecule with its complementary DNA in the single-stranded loop region of the MB. Different positions for linkage of biotin were tested: the loop sequence, the second base pair position of the fluorophore side of the stem, and the same position on the quencher side of the stem. The conformation wherein the biotin was linked to the quencher side of the stem minimized the effects biotin had on the MB's fluorescence, quenching and hybridization ability. Using an MB with an 18 base pair loop sequence, a spacer was inserted between biotin and the sequence. Biotin-dT was used to provide easy access for target DNA molecules hybridizing with the loop sequence, and to provide adequate separation, so as to minimize potential interactions between avidin and the DNA sequence.

Genomagnetic Nanocapturers

Figure 6:
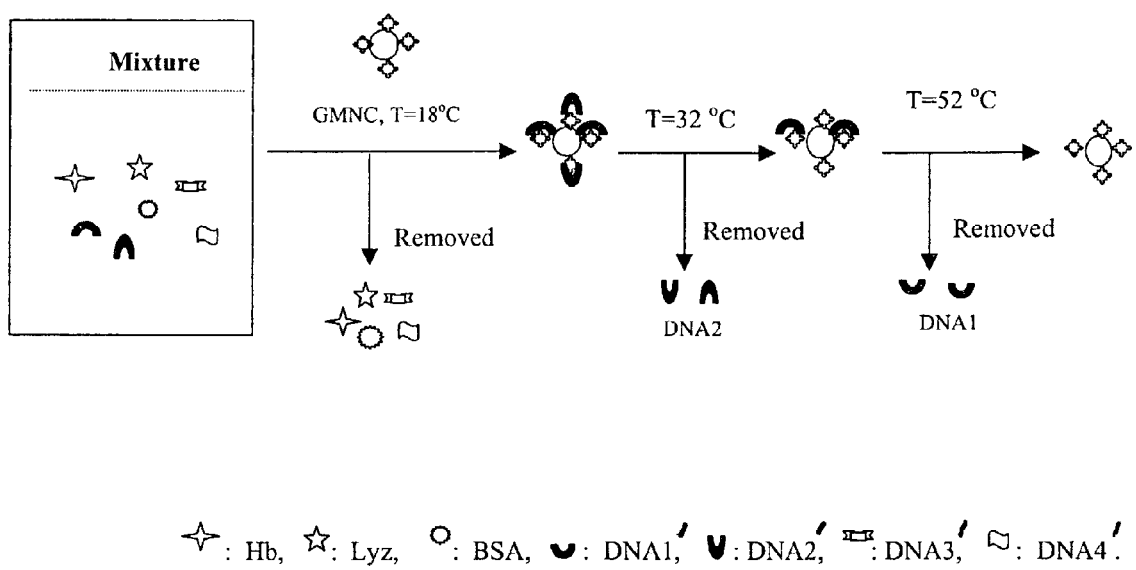
FIG. 6 is a schematic illustration of the steps involved in separating a polynucleotide of interest (DNA1') from a complex mixture of nucleic acids and proteins.

Also within the invention is a method of using MB-conjugated nanoparticles to isolate a particular target nucleic acid molecule from a sample, e.g., one including oligonucleotides differing from the target by just a single base or one containing a mixture of DNA and proteins. In one version of this method, a magnetic nanoparticle is conjugated with an MB that hybridizes to the target nucleic acid (e.g., under stringent hybridization conditions). These conjugated magnetic nanoparticles have been termed genomagnetic nanocapturers (GMNC). Referring to FIG. 6, the MB-GMNCs are added to the sample under conditions that allow for hybridization of the MB with the target nucleic acid (i.e., DNA1') and with targets differing by a single base (i.e. DNA2'), and for detection of the hybridized sequences by fluorescence imaging (see specific examples below). In another embodiment of this method, MB-GMNCs can be used to separate trace amounts of RNA (e.g., mRNA) from a complex mixture, including a cellular lysate. Following hybridization of the MB to the select DNA or RNA target, a magnet is then used to remove the MB-GMNCs bound to the target nucleic acid from the sample. The target nucleic acid can then be separated from the MB-GMNCs using conventional techniques for separating hybridized nucleic acids, e.g., by increasing the temperature or the salt concentration of the solution containing the MB-GMNCs. While the foregoing can be performed using MBs not conjugated to a fluorophore or quencher, the use of such conjugated MBs allows the separation process to be monitored by fluorescence analysis.

EXAMPLES

Example 1

Preparation of Doped Nanoparticles (A) Preparation of Eu/Bpy ($Eu^{3+}$/2,2'-dipyridyl)-doped silica nanoparticles in cetyltrimethylammonium bromide (CTAB)/n-hexane/n-hexanol (cosurfactant)/water water-in-oil microemulsions. 90 ml of a water-in-oil microemulsion stock solution was prepared by mixing together 2.916 g CTAB, 75 ml n-hexane, 15 ml n-hexanol and 880 µl water using a magnetic stirrer. 10 ml of the stock solution was equally divided into two 5 ml aliquots. 50 µl TEOS and 5 µl 0.1 M Eu/Bpy (aqueous solution) was added to one of the 5 ml aliquots and the mixture was stirred for 1 hr to form a TEOS/Eu/Bpy solution. 137 µl $NH_4OH$ was added to the other 5 ml aliquot and the mixture was stirred for 1 hr to form an $NH_4OH$ solution. The $NH_4OH$ solution was then added dropwise to the TEOS/Eu/Bpy solution and the resulting mixed solution was stirred overnight. The water to surfactant molar ratio of the mixed solution was 15 (water:surfactant). Eu/Bpy-doped silica nanoparticles were isolated in powder form by adding 25 ml of acetone to the microemulsion of the mixed solution, centrifuging the resultant mixture for 15 minutes at 10,000 RPM in a microcentrifuge to pellet the nanoparticles, the supernatant was removed and the remaining nanoparticles were washed several times with acetone or an ethanol/water solution to further remove surfactant and other microemulsion components. The washed nanoparticles were then dried over acetone.

(B) Preparation of Ru/Bpy [Ru$^{II}$(Bpy)$_3$]-doped Nanoparticles. 10 ml of a water-in-oil microemulsion was prepared by mixing 7.5 ml cyclohexane, 1.8 ml n-hexanol, 1.77 ml TX-100, 340 μl water and 140 μl 0.1 M Ru$^{II}$(Bpy)$_3$ (aqueous solution) for 1 hr with a magnetic stirrer. The resulting solution was then divided into two 5 ml aliquots. 100 μl TEOS was added to one aliquot and the mixture was stirred for 30 minutes to form a TEOS solution. 60 μl of NH$_4$OH was added to the other 5 ml aliquot and the mixture was stirred for 30 minutes to form a NH$_4$OH solution. The NH$_4$OH solution was then added to the TEOS solution dropwise for a period of 10 minutes and the resulting mixed solution was stirred overnight. Ru/Bpy doped silica nanoparticles were isolated as described above in Example 1A.

(C) Preparation of Tetramethylrhodamine (TMR)-doped Nanoparticles.

A water-in-oil microemulsion solution was prepared by mixing 1.77 ml of Triton X 100 (surfactant), 1.8 ml of n-hexanol (co-surfactant), 7.5 ml of cyclohexane (oil), and 0.48 ml of 1.2 mM TMR in acetic acid (water). The precursor (100 μl of TEOS) was added to the microemulsion solution, followed by stirring for 30 min. The silica polymerization reaction was completed by stirring for 24 hours. To break the microemulsion system and further separate the nanoparticles from the solution, 20 ml of acetone was added to the microemulsion solution. After sonicating and vortexing, the solution was centrifuged to obtain the TMR-doped nanoparticles. The resultant nanoparticles were washed four times with 95% ethanol and one time with acetone. After each wash, the nanoparticles were completely dispersed in the solution using sonication and stirring.

To clarify the function of acetic acid in the doping of the TMR molecules during the formation of nanoparticles, an inorganic acid, i.e., hydrochloric acid (HCl) was compared to acetic acid. Constant amounts of TMR were added to different concentrations of HCl to form the water pool. As was the case for pure water, using HCl in the water pool resulted in silica nanoparticles containing no TMR. This result demonstrated that the TMR trapped inside the silica matrix was not caused by pH changes, but was the result of TMR solubility in the organic acid.

Acetic acid also served as a catalyst for hydrolysis of TEOS during the synthesis of TMR-doped nanoparticles in the microemulsion system. The process of polymerization was improved by adding 60 μl of NH$_4$OH to the microemulsion system. To further lower the possibility of large particle formation, ethanol and acetone were used to wash the resultant nanoparticles after the synthesis process. Observation by TEM of TMR-doped silica nanoparticles made by the microemulsion method revealed that the final size of nanoparticles depended greatly on the size of the spherical water pool. By changing the ratio of the water to surfactant ($W_0$) value, different sizes of nanoparticles can be obtained. As an example, use of a $W_0$ value of 10, resulted in nanoparticles with a diameter of 60±4 nm.

Effect of concentration of acetic acid on the doping of TMR. The concentration of acetic acid in the water pool greatly affected the amount of TMR molecules trapped inside the nanoparticles. When the concentration of acetic acid was lower than 10.0 M, few TMR molecules were doped, as indicated by the low fluorescence intensities of the nanoparticles. When the concentration of acetic acid was higher than 10 M in the water pool, the amounts of doped TMR were greatly increased.

Effect of TMR concentration on fluorescence intensity of nanoparticles. The fluorescence intensity of TMR-doped nanoparticles was dependent on the number of TMR molecules doped inside the silica matrix. Due to self-quenching, the fluorescence intensities of the nanoparticles are not proportional to the number of dye-doped molecules. There was an optimum dye concentration for a particular size of nanoparticle with which maximal fluorescence intensity could be obtained. To determine the optimal concentration of TMR, TMR-doped silica nanoparticles were synthesized under conditions of varying the dye concentration from 0 to 4 mM with respect to the total volume of the water pool. Fluorescent intensities of the resultant nanoparticles were detected in solutions containing 0.1 mg/ml nanoparticles using a spectrofluorometer at 550 nm excitation and 575 nm emission. Results showed that highest fluorescence intensity of TMR-doped nanoparticles occurred at a concentration of 1.2 mM TMR. Further TMR molecule loading reduced nanoparticle fluorescence intensity due to the self-quenching of TMR molecules.

Amplification of fluorescent signals of TMR-doped nanoparticles. The extent of signal enhancement achievable with TMR-doped nanoparticles, relative to inorganic dye-doped nanoparticles, was determined. RuBpy-doped nanoparticle were synthesized as described above using the same microemulsion method. Fluorescence signals of nanoparticles both in solution and immobilized on a solid surface were detected using a microscope and a sensitive spectrofluorometer. The two kinds of nanoparticle samples were processed in the same way.

For the detection in solution, several concentrations of nanoparticles ranging from 0.1 μg/ml to 1 mg/ml were analyzed using a spectrofluorometer. Based on the density of the nanoparticles, the number of nanoparticles in each sample was calculated, to obtain the average fluorescence signal of a single nanoparticle. The results showed that the fluorescence intensity of one TMR nanoparticle was 40 times higher than one RuBpy nanoparticle.

A second comparison, i.e., of one TMR-doped nanoparticle with one TMR molecule, was carried out in a similar manner. This result demonstrated a 15,000× signal enhancement for the TMR nanoparticle vs. the TMR molecule. Further confirmation of the amplification was obtained using a different experimental method. The fluorescence intensities of single nanoparticles were detected based on the fluorescent images on a glass surface using a microscope. With frequent sonicating and vortexing, the nanoparticle solutions were diluted to such a point that there was little aggregation of the nanoparticles in the samples (result verified by SEM). Thus each fluorescent spot in the microcopy images corresponded to a single nanoparticle. The average fluorescence intensity of one TMR nanoparticle was statistically obtained using ImageJ software, and results obtained correlated well with the spectrofluorometric results.

Stability of TMR-doped nanoparticles. To verify the photostability of the nanoparticles, pure TMR molecules were compared with TMR-doped silica nanoparticles in solution. Following continuous irradiation with 550 nm light for 20 minutes, the fluorescence intensity of the pure dye molecules was reduced by 85%, whereas the fluorescence intensity of nanoparticles remained constant.

Long-term stability of TMR-doped nanoparticles in aqueous solution. This analysis focused on the potential leakage of dye molecules from the silica matrix immersed in solution for extended periods. TMR-doped nanoparticles were immersed in water solution for 3 days and 7 months, respectively, and the fluorescence intensities of the solutions were subsequently detected. The samples were centrifuged to separate TMR-doped nanoparticles from the supernatant containing any TMR molecules having leached out from the nanoparticles. The precipitate was resuspended in water to its original volume and fluorescence intensity was detected. Comparison of fluorescence intensities before and after centrifugation showed that there was no leakage of TMR molecules from the matrix after 3 days in aqueous solution. After 7 months of storage, only 8.5% TMR leaked from the silica matrix. These results clearly showed that once TMR molecules are trapped inside the silica matrix, they remain firmly embedded within the nanoparticles.

(D) Preparation of R6G-doped Nanoparticles. Three ml of a 1 mM solution of the dye in ethanol was mixed with 1.0 ml phenyltriethoxysilane (PTES). Hydrochloric acid or ammonium hydroxide was added to the resulting solution to start the hydrolysis of the PTES. Completion of the reaction was indicated by the formation of a one-phase system after a few hours. Hydrolyzed solution (0.5 ml) was then added with 100 μL TEOS, dissolved to 5.0 ml with ethanol and further reacted with ammonium hydroxide via the Stöber process (Stöber et al., J Colloid and Interface Sci. 26:62, 1968). The reaction was performed for an hour at 0° C. with continuous sonication and frequent vortexing. Nanoparticle formation was terminated by addition of an excess amount of acetone to the mixture.

TEM and SEM demonstrated that the above process resulted in the production of organic dye-doped nanoparticles in the vicinity of 100-nm diameter. Allowing the reaction to proceed for more than 12 hours resulted in particles in the micrometer range.

The amount of PTES is an important factor for the entrapment of R6G in the nanoparticles. An increase in the amount of PTES resulted in a corresponding increase in the yield of doped dye molecules, seen as an increase in the fluorescence intensity. Fluorescence intensity comparison was done for samples with different PTES:TEOS volume ratios, (1SR1) 0.25:1, (1SR2) 0.5:1, and (1SR3) 1:1). It was determined that there was a limiting ratio at which precipitate began to be formed. Too high a concentration of PTES yielded nanoparticles with high hydrophobicity. A 2:1 or lower ratio was found to yield water-soluble nanoparticle products. The effect of the concentration of R6G in the solution was determined under conditions of constant amounts of PTES and TEOS. Increased fluorescence intensity was observed with increased nominal concentration of R6G. The fluorescence intensities of 1 mg samples dispersed in 1 ml solution were compared to various concentrations of pure R6G. The amounts of R6G trapped in the nanoparticles were calculated to be less than 1% based on a calibration curve established using pure R6G molecules. With a 1% R6G concentration inside the nanoparticle, the nanoparticles showed higher luminescence intensity than RuBpy-doped nanoparticles which optimally contain 20% of the dye.

Once the dye molecules were trapped inside the silica matrix, the nanoparticles were washed with acetone and water. The doped dye molecules showed minimal leakage in aqueous solutions. Samples were immersed in solution for 3 days and the fluorescence of the solutions before and after centrifugation were compared. The 3-day aqueous solution was centrifuged to separate the dye-doped nanoparticles from the supernatant. The precipitate was again resuspended in water to the original volume, and fluorescence intensities of the original solution and the resuspended precipitate were compared. No significant difference in the intensities were observed, indicating that most of the dye molecules were kept trapped in the matrix of nanoparticles, presumably due to the hydrophobic nature of the PTES.

To assess photobleaching, the photostability of the pure dye and the dye-doped nanoparticles were compared. The samples were continuously illuminated for 1000 seconds and fluorescence intensities were monitored using solid-state spectrofluorometry. To minimize experimental instability, the samples were sandwiched between two coverslips during monitoring. Results showed that the intensity of the pure R6G decreased rapidly, while the fluorescence intensity of the R6G inside the nanoparticle did not change significantly under the same conditions. The much-improved photostability of the organic dye in the nanoparticles minimizes photobleaching of bioassays and thereby increases the accuracy of bioanalysis using these nanoparticles.

Example 2

Cellular Detection Using Antibody-Conjugated Nanoparticles

Silica-coated nanoparticles were used in several applications to show their usefulness for cellular recognition and marking. In one embodiment, silica-coated nanoparticles were conjugated with antibodies. Nanoparticles prepared as described in Example 1(A) were derivatized with antibodies by first silanizing the particle surfaces with DETA, a silanization agent that attaches the primary amine group to silica surfaces. Using fluorescamine, a non-fluorescent molecule that becomes highly fluorescent upon reacting with the primary aliphatic amine group (Cordek et al., 1999; Chung, 1997), the presence of amine group on the surface of the nanoparticles was confirmed. After surface silanization with DETA, an antibody (mouse anti-human CD10) was immobilized onto the silanized silica surface using the cyanogen bromide (CNBR) method. Dye-doped particles were prepared as described above, dried, and suspended in 9.0 ml 2 M sodium carbonate solution (activation buffer) using ultrasonication. A solution of CNBR in acetonitrile (1.0 gm of CNBR dissolved in 0.5 ml acetonitrile) was then added dropwise to the nanoparticle suspension (10 mg/ml) under stirring for 5 minutes at room temperature. The resulting CNBR-activated particles were washed twice with ice-cold water and twice with PBS buffer (pH 8.0). 40 μl of the antibody diluted in PBS buffer (pH 8.0) was then added to the surface-modified particles, and stirring was continued for 24 hours at 4° C. The resulting antibody-derivatized nanoparticles were then treated with 10 ml of 0.03 M glycine solution for 30 minutes to block any remaining reactive sites. The final product was washed, re-suspended in PBS buffer (pH 8.0) and stored at 4° C. for future use. No change in the optical and spectroscopic properties of the nanoparticles was observed.

Mononuclear lymphoid cells (about 2 million cells/ml) were obtained as a suspension in cell culture medium. The cell suspension was incubated for 2 hours with the anti-CD 10 immobilized nanoparticles. After incubation, the cell suspension was imaged with both optical microscopy and fluorescence microscopy. The microscopic analysis revealed that most of the cells were labeled (indicated by the bright emission of the dye-doped particles). The optical images correlated well with the fluorescence images. In control experiments using non-antibody derivatized dye-doped nanoparticles, no labeling of cells was observed. In the labeled cells, the signal-to-noise ratio (i.e., the ratio between the intensities of the bright and the dark areas in the fluorescence image) was over 500.

Example 3

Methods Using Protein-Conjugated Nanoparticles

PDGF-conjugated nanoparticles. To assess the usefulness of nanoparticles for detection of platelet-derived growth factor (PDGF) receptors, PDGF was conjugated with TMR-nanoparticles (prepared as described in Example 1) by means of covalent immobilization onto the nanoparticles. The surfaces of TMR-doped silica nanoparticles were first chemically modified. To form amine-functionalized groups on the nanoparticle surfaces, silica nanoparticles were reacted with 1% DETA in 1 mM acetic acid for 30 min at room temperature, with continuous stirring. The amine-functionalized nanoparticles were thoroughly washed 3 times in distilled, deionized water. After washing with DMF, the nanoparticles were reacted with 10% succinic anhydride in DMF solution under $N_2$ gas for 6 hours with continuous stirring. Following a thorough water wash, the nanoparticles were activated, using 100 mg/ml of EDC and 100 mg/ml of NHS in MES buffer (pH 6.8), for 25 minutes at room temperature with continuous stirring. Water-washed nanoparticles were dispersed in 0.1 M PBS (pH 7.3). To covalently immobilize PDFG onto the nanoparticle surface, nanoparticles were reacted with 10 nM PDGF for 3 hours at room temperature with continuous stirring to form the resultant conjugates of nanoparticle-protein followed by washing in the PBS buffer. To reduce the effects of non-specific binding in subsequent reactions, the protein-conjugated nanoparticles were reacted with 1% BSA and washed in 0.1 M PBS (pH 7.3) before being used.

Binding of the PDGF-nanoparticles was tested using HTB-26, a breast cancer cell line. For these assays, suspensions of HTB-26 cells were incubated with PDGF-TMR-nanoparticles for 30 min at 37° C. with 5% $CO_2$. Results, analyzed by optical and fluorescence microscopy, revealed the brightly labeled cells indicating the presence of PDGF receptors on the HTB-26 cells, in cells incubated with PDGF-TMR-nanoparticles. In contrast, cells incubated with TMR-nanoparticles without PDGF were not fluorescent. These results showed that the fluorescent labeling of the cells was due to the binding of the PDGF-TMR-nanoparticles to PDGF receptors on the cell surface. These results provide a clear example of an application, involving receptor binding, of TMR-doped nanoparticles as highly fluorescent and photostable biomarkers for cellular studies. In another example of this method, adenocarcinoma cells (MDA-MB-231) expressing PDGF receptors were incubated with PDGF-conjugated TMR-doped nanoparticles. Fluorescence microscopy again revealed that the surfaces of the cells bound the PDGF-conjugated TMR-doped nanoparticles.

GDH-conjugated nanoparticles. R6G doped nanoparticles were tested as biosensors for glutamate detection by immobilizing an enzyme, i.e., glutamate dehydrogenase (GDH), onto the nanoparticle surfaces. GDH was immobilized onto the nanoparticles using a modification of described methods (Cordek J. et al., Anal. Chem. 71: 1529, 1999; Qhobosheane S. et al, Analyst 126:1274, 2001). Briefly, for bioconjugation with the enzyme, the nanoparticles were modified with a 2% solution of an aminosilane, $N^1$-[3-(Trimethoxysilyl)propyl] diethylene triamine, in 1 mM acetic acid. The resulting nanoparticles were further treated with a bifunctional crosslinker, glutaric dialdehyde, before subsequent conjugation to an enzyme, glutamate dehydrogenase (GDH). Adequate washing followed each step. An enzymatic reaction, $NAD^+$+glutamate→NADH+α-ketoglutarate, was used to test the activity of the GDH molecules immobilized on the nanoparticles. The fluorescence of NADH was monitored for the analysis of glutamate.

BSA-coated nanoparticles to detect an immobilized analyte. Avidin was physically adsorbed to the surface of silica-coated, R6G-doped nanoparticles and glass plates. The avidin was then cross-linked with glutaraldehyde and stored in Tris-HCl buffer. The coated glass plate was treated with two different concentrations of biotinylated bovine serum albumin (BSA). Each BSA molecule had 9 biotin molecules on average. Biotin-avidin interaction was checked by allowing the avidin-coated nanoparticles to bind with the available biotin molecules on the glass plate. The experiment was performed by fluorescence microscopy using filter sets selective for the 520 nm excitation and 550 nm emission of rhodamine 6G. Increasing numbers of nanoparticles adhered to glass surfaces containing the highest concentration of biotinylated BSA (2 mg/ml), whereas little binding was observed on the control glass containing unmodified BSA.

Example 4

Detection of Nucleic Acids

Ru/Bpy-doped silica nanoparticles were used as probes for detecting a specific DNA molecule. An overview of this method is shown in FIG. 4, wherein three different oligonucleotides (i.e., DNA1, DNA2, and DNA3) were used in a sandwich assay. DNA1, a biotinylated capture DNA, was immobilized on an avidin-coated glass substrate. DNA2, the target DNA was then contacted onto the substrate under conditions which promoted hybridization. Dye-doped silica nanoparticles conjugated with DNA3 were also added to the substrate. DNA1 and DNA3 contain nucleotide sequences complementary to different portions of DNA2, the target DNA. An inverted microscope was used to detect luminescent signals, and SEM was used to confirm the binding of the nanoparticle probes to the substrate surface.

DNA immobilization on quartz glass substrates. Coverslips cleaned by overnight immersion in 10 M NaOH were incubated for 12 h in a 1 mg/ml avidin (Molecular Probes, Eugene, Oreg.) solution in 10 mM phosphate buffer (pH 7.0). The avidin layer was stabilized by cross-linking with glutaraldehyde (Sigma Chemical Co., St. Louis, Mo.) (1% in 100 mM potassium phosphate buffer for 1 h at room temperature) and subsequent incubation in 1 M Tris-HCl (pH 7.5). 250 nL aliquots of 20 μM biotinylated DNA1 (5' TAA CAA TAA TCC T 3'; SEQ ID NO:1) (IDT, Coralville Iowa) were spotted onto the substrate which was then incubated for 12 h in a humidified chamber.

DNA immobilization on nanoparticle-probe. A 10 mg sample of Ru/Bpy-doped silica-coated nanoparticles was incubated in 1 ml of the avidin solution (Fang et al., Anal. Chem. 72: 747A, 2000). The avidin coating was cross-linked with 1% glutaraldehyde, and the nanoparticles were incubated in Tris-HCl solution. The nanoparticles were then incubated for 12 h in 1 ml of 20 μM of DNA3 to immobilize the DNA3 (5'TAT CCT TAT CAA TAT T 3'; SEQ ID NO:2) to the surface of the nanoparticles. Stringent washing and centrifugation followed each step. The resulting nanoparticles were resuspended at a final concentration of 0.5 mg/ml when the DNA3 concentration for incubation was 1 μM.

DNA hybridization. Aliquots of the target solution, DNA2 (5' GGA TTA TTG TTA AAT TTA GAT AAG GAT 3'; SEQ ID NO:3) (IDT, Coralville Iowa), were warmed to 50° C., placed over the spots of DNA1 immobilized on the substrate and incubated for 4 hours. After stringent washing with buffer, DNA3-conjugated nanoparticles were added to the substrate and allowed to hybridize in a humidified chamber for 4 hours. Stringent washing followed each step. Incubations were performed. Varying concentrations ranging from $10^{-12}$ to $10^{-6}$ of target DNA2 were analyzed. Equal concentrations of probe DNA and capture DNA were used in all experiments.

Optical testing and imaging. Luminescence images were obtained using an inverted fluorescence microscope (Olympus, model IX708F) equipped with an intensified charge coupled device (ICCD). SEM images were taken using an Hitachi S-4000 FE-SEM. Concentration dependent luminescence intensity data were used to evaluate the detection limit. Selectivity experiments were performed in a similar manner. Luminescence signals from both complementary target and one-base mismatched DNA were compared.

Using the methods described above, DNA1 was immobilized on an avidin-coated glass substrate. The immobilized DNA1 was then allowed to hybridize to one end of DNA2. The unhybridized 15 bases of DNA2 were then hybridized with biotinylated DNA3 attached to Ru/Bpy-doped silica-coated nanoparticles. The substrate surface was imaged after washing away any unhybridized DNA probe and physically adsorbed nanoparticles. Both fluorescence and SEM imaging confirmed that nanoparticles were attached to the substrate surface, indicating that hybridization of the three different DNAs had occurred.

To check the effect of temperature on the hybridization process, the foregoing assay was repeated at 25° C., 35° C., 45° C., and 55° C. Temperature equilibrium was achieved using a thermostat control. The luminescence intensity increased with increase in temperature up to 45° C., above which a decrease in the intensity was observed. In most of the experiments discussed below, 25° C. was used for convenience.

Highly sensitive analysis of DNA target. The concentration dependence of the signal was also tested using fluorescence imaging techniques for different ranges of target DNA (DNA2), i.e., concentrations from $10^{-12}$ M to $10^{-6}$ M. Calibration curves for $10^{-11}$ M to $10^{-9}$ M and for $10^{-9}$ M to $10^{-6}$ M were plotted. Using imaging software, the average signal intensities for each sample were obtained. Overall, there was an excellent linear relationship between the target DNA concentration and the luminescent signal except for the highest concentration range (1 μM and up). Possible saturation was observed at $5\times10^{-7}$ M and $1\times10^{-6}$ M. This concentration dependence was evident on both fluorescence luminescence images and SEM images. The SEM images showed an increase in nanoparticle density as the concentration of the target DNA was increased. Concentrations of the capture DNA and probe DNA were kept constant in these experiments. Notably, the detection limit for this assay was $3\times10^{-12}$ M.

Figure 7:
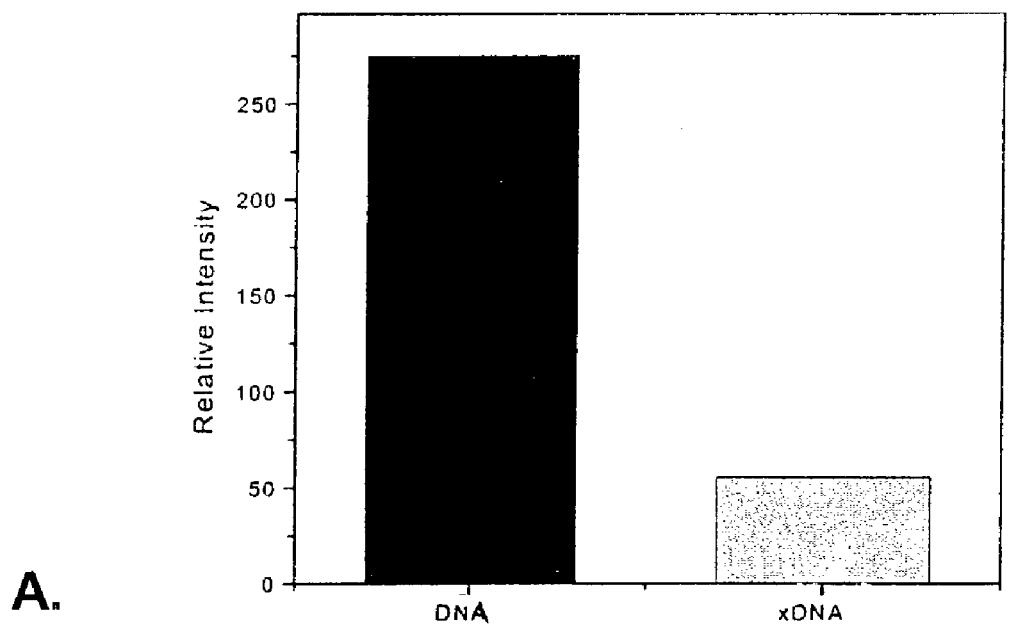
FIG. 7 is two graphs showing one-base mismatch selectivity of a method for detecting a nucleic acid of the invention. (A) signal from a perfectly complementary nucleic acid versus that from a single base mismatch nucleic acid. (B) signal from an A-T single base mismatch versus that from a G-C single base mismatch.
Figure 7:
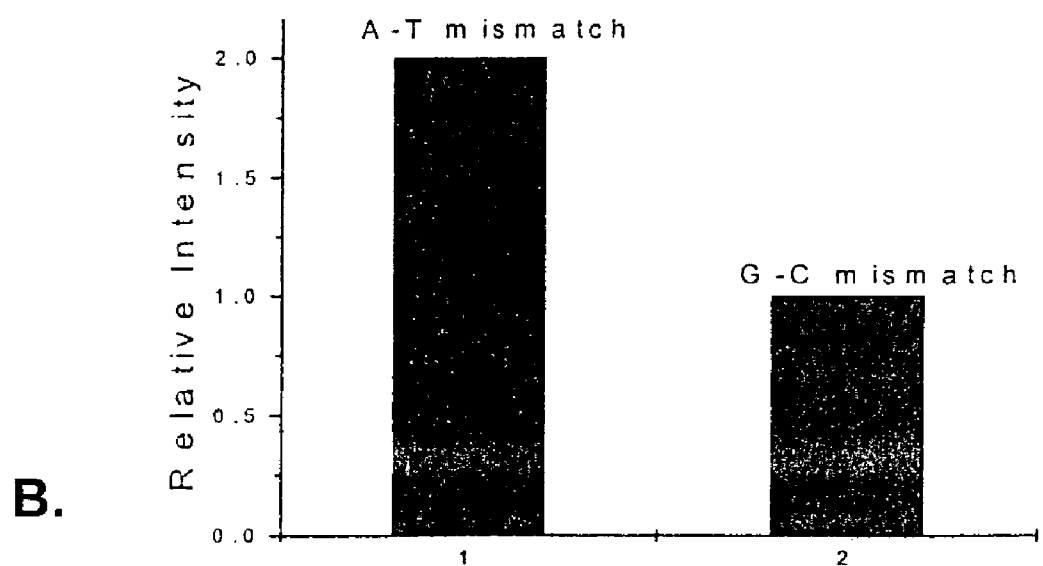

Differentiating between A-T and G-C mismatch. The method described above is so sensitive that it can distinguish a single base mismatch in a 27 bp linear DNA. As shown in FIG. 7A, there is a large difference in luminescent intensity between that obtained from the complementary DNA (i.e., DNA2) and from a one-base mismatched target DNA, i.e., xDNA2 (5' GGA TAA TTG TTA AAT TTA GAT AAG GAT 3'; SEQ ID NO:4) of equal concentration. Moreover, referring to FIG. 7B, the amplification in signal provided by the dye-doped nanoparticles was so great that even an A-T mismatch could be distinguished from a G-C mismatch.

Example 5

Detection and Separation of Nucleic Acids Using Immobilized Molecular Beacons

Chemicals and Apparatus. All biochemicals were purchased and used as received. Lysozyme (Lyz), hemoglobin (Hb) and BSA were purchased from Sigma (St. Louis, Mo.). Ferric chloride, ferrous chloride, Triton X-100, isooctylphenylether, 4-$(C_8H_{17})C_6H_4(OCH_2CH_3)_nOH$, n~10), and TEOS were purchased from Aldrich Chemical Co. Inc. (Milwaukee, Wis.). Cyclohexane, n-hexanol, sodium hydroxide were obtained from Fisher Scientific Co. (Pittsburgh, Pa.). Distilled deionized water (Easy Pure LF) was used for the preparation of all aqueous solutions in the synthesis of magnetic nanoparticles. An FS20 ultrasonicator (Fisher Scientific Co.), centrifuge 5810 R (Eppendorf), Hitachi H-7000 Transmission Electron Microscope (Japan) and MPMS-5S Superconducting Quantum Interference Device (SQUID) Magnetometer were used for the synthesis and characterization of magnetic nanoparticles. A Fluorolog TAU-3 spectrofluorometer (Jobin Yvon-Spex, Instruments S.A., Inc.) was used to detect fluorescence intensity at different temperatures.

(A) Preparation of Biotinylated MBs for Attachment to Surfaces.

Synthesis of a biotinylated MB. An MB suitable for attachment to a surface was designed based on an avidin-biotin linkage. The nucleotide sequence of the MB was designed with a total of 28 base pairs, of which 18 base pairs were the loop sequence of interest. Five base pairs, complementary to each other, formed the stem. The selected fluorophore was TMR and the quencher was DABCYL (both from Molecular Probes, Eugene, Oreg.). The target DNA had the following sequence: 5'-TTC CTT CCT GGG CAT GGA-3' (SEQ ID NO:5). The biotinylated MB designed to hybridize with the target DNA had a molecular weight of 10076, and the following sequence: 5'-GCA CGT CCA TGC CCA GGA AGG AAC G(Biotin dT)G C-3' (SEQ ID NO:6) and was conjugated to TMR and DABCYL at its 5' and 3' ends, respectively.

The biotinylated MB was synthesized using DABCYL-CPG (controlled pore glass) as the starting material. The synthesis involved four important steps. First, a CPG solid support was derivatized with DABCYL and used to start the synthesis at the 3' end. The remaining nucleotides were added sequentially, using standard cyanoethylphosphoramidite chemistry, including a biotin-dT residue that had biotin attached to the C5 carbon of the ring (Glen Research). The purpose of the biotin was to provide a link to avidin molecules bound to a surface. Second, the 5' end of the nucleotide was conjugated to a $(CH_2)6$-NH linker arm, producing a primary amine group at the 5' end. The primary amine group at the 5' end was linked to the phosphodiester bond by a six carbon spacer arm. There is a trityl protecting group at the ultimate 5'-end that protects the amine group. Third, the oligonucleotide was purified by reverse phase HPLC and converted to a sodium salt form. Finally, the purified oligonucleotide was labeled overnight with TMR in a sodium bicarbonate/DMF buffer. The 5' trityl group was removed by treatment with acetic acid for one hour, followed by drying overnight under vacuum. After labeling, the excess dye was removed by gel filtration chromatography on Sephadex G-25. The oligonucleotide representing the designed biotinylated MB was then purified by reverse phase HPLC and the main peak was collected.

Hybridization study using biotinylated MBs in solution. The newly synthesized biotinylated MB was used to assess its DNA hybridization properties in solution. Hybridization properties were tested using fluorescence measurements performed on a SPEX Industries F-112A spectrophotometer. A sub-micro quartz cell was used for the hybridization experiment. Three solutions were prepared containing: MB alone, MB and a 5-fold molar excess of its complementary target DNA, and MB with a 5-fold molar excess of a non-complementary DNA. The final concentration of MBs in all three solutions was 50 nM. Solutions (200 μl) were incubated for 20 minutes in a buffer solution containing 20 mM Tris-HCl, 50 mM KCl, and 5 mM $MgCl_2$ (pH=8.0). Emission spectra were recorded at room temperature with excitation at 515 nm.

The biotinylated MBs hybridized in solution showed a more than 10-fold enhancement in fluorescence signal when reacted with the target DNA molecules. The solution with the non-complementary DNA showed no enhancement under the same conditions. Hybridization dynamics of the biotinylated MBs were compared with those obtained using MBs without biotin, and similar results were obtained in both cases.

(B) Preparation and Use of MBs Immobilized on a Solid Plate.

Immobilization of biotinylated MBs on a silica plate. To prepare a silica-coated surface, silica glass coverslips were first cleaned in a 1:1 HCl:aqueous solution for 2 hours. After thorough rinsing with water, the coverslips were placed in a 10 M NaOH solution overnight, and again rinsed with water. The treated coverslips were then incubated in an avidin solution (0.1 mg/ml, 10 mM phosphate buffer, pH 7.0) for 12 hours. The physically adsorbed avidin was stabilized by cross-linking in 1% glutaraldehyde buffer solution for 1 hour, followed by incubation in 1M Tris/HCl (pH 6.5) for 3 hours. The avidin-coated coverslips were then washed with phosphate buffer and dried under nitrogen. To create an MB-coated surface, a drop of a biotinylated MB solution ($1 \times 10^{-6}$M in the buffer) was added to an avidin-coated coverslip. The avidin-biotin binding time ranged from a few minutes to half an hour. The coverslips were then washed in hybridization buffer (20 mM Tris-HCl, 50 mM KCl, 5 mM $MgCl_2$, pH 8.0) to remove any unbound MBs. The binding process was fast and efficient. Within a few minutes, coverage equilibrium was reached. Immobilized MBs remained attached to the avidin-coated surface even after immersion in buffer solution for several days.

Hybridization study using biotinylated MBs immobilized on a plate. MB fluorescence intensities were monitored under different hybridization conditions. Monitoring of the fluorescence signal was performed using a fluorescent microscope, an ICCD, an argon ion laser and an optical fiber probe for light transmission to the microscope stage as described previously (Fang, X and Tan, W, Anal. Chem. 71, 3101-3105, 1999). An excitation laser beam, 514 nm, was first directed to the optical fiber probe with a 50 μm core and was then coupled to a prism which was put on the stage of the microscope. An evanescent field was generated on the surface of the prism which was sandwiched with the MB-immobilized silica plate glass, and used to excite the immobilized MBs. Fluorescent signals thus produced were collected by an objective and directed to the ICCD.

When the MBs immobilized on the silica plate interacted with their complementary DNA target molecules, a double-stranded DNA duplex was formed, thereby causing the fluorescence signal from the fluorophore attached to the MB to increase. MB probe testing was carried out with different concentrations of complementary DNA molecules, ranging from 5 nM to 600 nM. The results indicated that the MB-immobilized plate could be used to detect target DNA molecules in the nanomolar range. When non-complementary DNA molecules were used, there was no increase in fluorescence signal. Additional experiments showed that the MBs immobilized on the plate could be regenerated after hybridization, thereby allowing for multiple reuses of the plate for DNA detection and interaction studies.

(C) Preparation of MBs Immobilized on Nanoparticle Surfaces.

Design and synthesis of a biotinylated MB. For use in studies of MBs immobilized on the surface of nanoparticles, an MB was designed and synthesized, using methods described above, having a 15-nucleotide loop and 5-nucleotide arms. The loop sequence, 5'-ATC AAT ATT TAA CAA-3 (SEQ ID NO:7), was complementary to a DNA encoding anthrax lethal factor. Four different DNA target sequences were prepared for DNA hybridization studies with the MB: DNA1': 5'-TTG TTA AAT ATT GAT-3 (SEQ ID NO:8); DNA2': 5'-TTA TTA AAT ATT GAT-3' (SEQ ID NO:9); DNA3': 5'-TAG TTA TAA ATT GTT-3'(SEQ ID NO:10) and DNA4': 5'-TAG TTA TAA ATT ATT-3' (SEQ ID NO:11). Fluorescein was utilized as the fluorophore and DABCYL as the quencher in this biotinylated MB. The MB synthesized according to the above design was used for immobilization on the surfaces of magnetic nanoparticles.

Immobilization of MBs on magnetic nanoparticle surfaces. Silica-coated magnetic nanoparticles were synthesized using the water-in-oil microemulsion method described above. The microemulsion was prepared using Triton X-100 surfactant. $FeCl_2$ and $FeCl_3$ were used to form iron oxide nanoparticles. The silica layer was formed by adding TEOS to the microemulsion. The MBs were immobilized on the surfaces of the magnetic nanoparticles via an avidin-biotin linkage. Briefly, avidin was first coated on the surfaces of the nanoparticles by incubating silica-coated magnetic nanoparticles in an avidin solution (2 mg/ml in 10 mM phosphate buffer, pH=7.3) for 14 h in a refrigerator. The avidin-coated nanoparticles were subsequently washed three times with 0.5 ml of buffer. The avidin layer was stabilized by cross-linking the coated nanoparticles with 1% glutaraldehyde in 100 mM potassium phosphate buffer for 1 h at room temperature. The avidin-coated nanoparticles were then incubated in the Tris-HCl buffer for 3 h in a refrigerator after being washed three times with 0.5 ml of 1 M Tris-HCl buffer (pH=7).

To immobilize the MBs on the surfaces of the avidin-coated magnetic nanoparticles, the nanoparticles were incubated with a solution containing $1.0 \times 10^{-6}$ M biotinylated MB for 12 h in a refrigerator. Each avidin molecule has four biotin binding sites. To ensure that each exposed biotin group was bound to an avidin molecule, avidin was used in excess. The nanoparticles were washed three times with 20 mM Tris-HCl/5 mM $MgCl_2$ buffer (pH=8) and the magnetic nanoparticles with surface-conjugated MB (MB-GMNCs) were stored under refrigeration for future use.

The efficiency of the MB immobilization procedure was investigated by comparing fluorescence intensities of the MB incubation supernatant solution, washing solutions, and the MB-GMNCs. To each of these three solutions, a six-fold excess of complementary DNA1' was added. The addition of DNA1' to the MB reduced the fluorescence quenching due to fluorescence energy transfer between fluorescein and DABCYL molecules. The GMNC sample was much more fluorescent than either the supernatant or washing solutions indicating that most (92.2% in one experiment) of the MB were conjugated to the GMNC, and that the MB bound to the GMNC retained the ability to bind target DNA.

(D) Use of MB-GMNCs for Separation and Collection of Target DNAs.

Design and steps of the separation procedure. MB-GMNCs prepared as described above were tested for their ability to selectively capture target DNAs from a complex mixture of polynucleotides, in some cases in the presence of proteins. Referring to FIG. 6, the overall design and steps in the separation process are illustrated in schematic form. In a test incorporating both DNA and protein in the mixture, the selected mixture contained trace amounts of target DNA1' and DNA2', large amounts of random DNA3' and DNA4' (at 100-fold concentration) and several proteins at 1000-fold concentration, i.e. BSA, Hb and Lyz. DNA1' was a perfectly complementary target to the loop sequence of the MB while DNA2' was a single-base mismatched sequence.

To begin the test, MB-GMNCs were added to the complex DNA-protein mixture for 30 min at 18° C. to permit binding of the DNA targets to the MB-GMNCs. The separation process involved three steps. The first step was separation and retrieval of target sequences (DNA1' and DNA2') from the complex mixture. DNA1' and DNA2' specifically hybridized with the MB on the GMNC surfaces while the random DNA sequences and proteins did not. When the mixture was exposed to a magnet, the GMNCs carrying trace amounts of DNA1' and DNA2' were collected and separated from the mixture.

The second step was the separation of DNA1' from DNA2'. Separation of DNA1' and DNA2' was based on differences in the melting temperatures of the duplexes formed with the MBs. A 20 μl volume of 20 mM Tris-HCl/5 mM $MgCl_2$ buffer was added to the GMNCs. DNA1' and DNA2' were separated by raising the GMNC buffer temperature to 32° C. for 15 min. At this temperature, DNA2' completely dissociated from the GMNC, while DNA1' remained bound on the GMNC surface. The solution was then re-exposed to a magnetic field, and GMNCs with bound DNA1' were removed. The supernatant contained DNA2'. Thus DNA1' and DNA2' were separated both from the mixture and from each other.

The final step in the separation was retrieval of DNA1' from the MB-GMNCs. A 20 μl volume of 20 mM Tris-HCl/5 mM $MgCl_2$ buffer was added to the MB-GMNC with bound DNA1'. The temperature of the solution was raised to and fixed at 52° C. for 15 min, resulting in the complete dissociation of DNA1' from the MB-GMNCs. The MB-GMNCs were then removed from the solution using an applied magnetic field.

Selection of melting temperatures for DNA separation and collection. The second step of the separation procedure shown in FIG. 6 involves separation of closely related DNA sequences by virtue of differences in the melting temperatures of the DNA duplexes formed between the MBs and the target DNA sequences. Tests were conducted to determine the appropriate temperatures for differential separation of perfectly matched, i.e complementary DNA sequences (e.g. DNA1'), and one-base mismatched DNA sequences (e.g. DNA2') bound to the surfaces of the MB-GMNCs. This entailed determining the temperature range over which hybridization of the MB with a complementary sequence (DNA1') was stable, whereas hybridization to a one-base mismatched sequence (DNA2') was not. Using a linear DNA probe with the same loop sequence as the MB, it was found that the melting temperature difference between the complementary and one-based mismatched DNA was 7° C. By contrast, using the same sequence as the loop of the MB, the temperature differential was 21° C.

Figure 8:
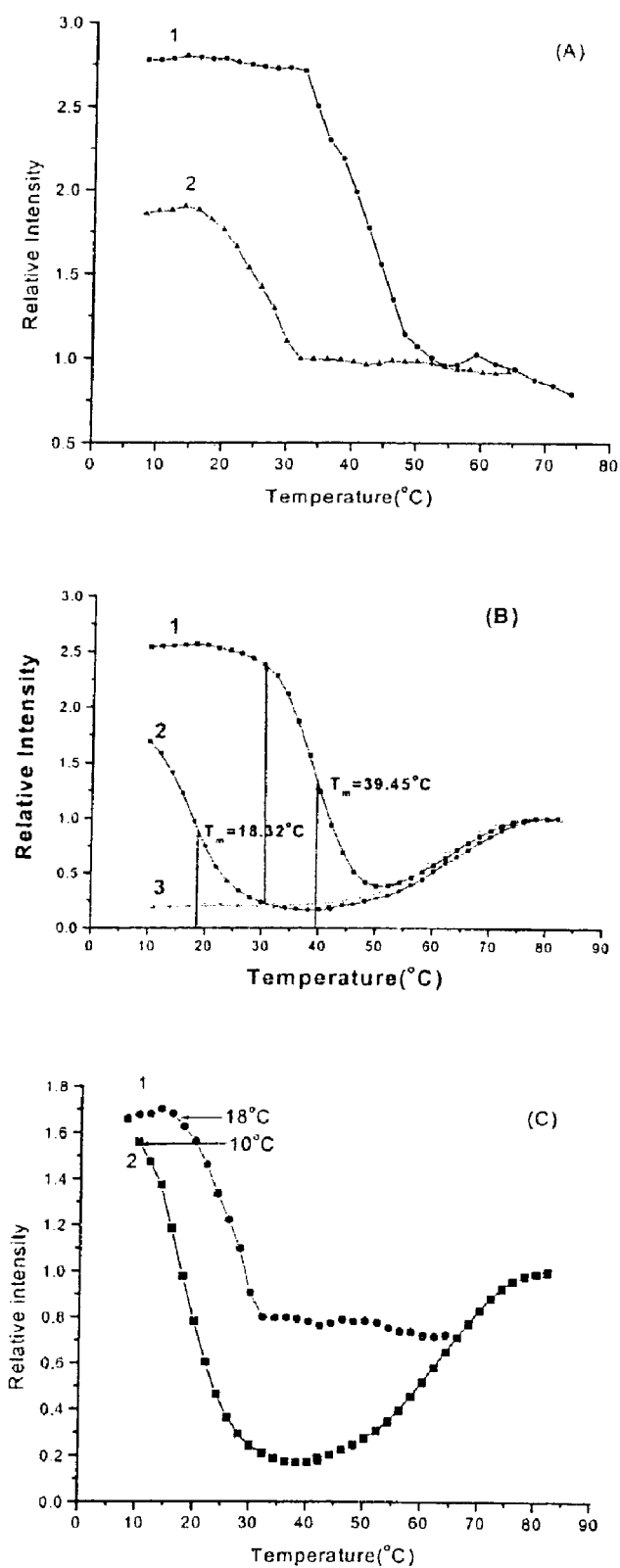
FIG. 8 is a series of graphs showing melting temperature profiles of MBs duplexed to target DNA sequences under conditions of MB immobilization on genomagnetic nanocapturers (MB-GMNCs), or free in solution.

The effect of temperature on binding of DNA1' and DNA2' to MBs, with and without immobilization on GMNCs, was further investigated over a range of temperatures. The results are shown in FIG. 8. FIG. 8A shows results with MBs immobilized on GMNCs. A 6-fold excess of DNA1' (0.6 μM, curve 1) or DNA2' (0.6 μM, curve 2) was added to a solution containing MB-GMNCs. Fluorescence intensities of the solutions were detected as a function of temperature. The temperature was slowly increased from 8° C. to 75° C., in steps of 2° C. with a 5 minute duration for each temperature interval in order to achieve equilibrium. As seen in FIG. 8A, at low temperatures both DNA1'-MB and DNA2'-MB duplexes on the GMNC surfaces fluoresced well, indicating that the MBs were in the open (linear) configuration due to hybridization. As the temperature increased, the fluorescence emission decreased in both samples. However, even at the lowest temperature, the one-base mismatched sample (DNA2') had considerably lower fluorescence intensity compared to the complementary DNA (DNA1'). The mismatched duplex became unstable over 18<C and completely dissociated at 32° C. In contrast, the DNA1' duplex was still stable with only 3% dissociation at 32° C. Therefore, it was possible to separate DNA1' from DNA2' by raising the temperature to 32° C. At this temperature, 100% of DNA2' was separated with only 3% DNA1' dissociated into the solution.

Melting temperature profiles of MB duplexes not conjugated to GMNC (i.e., in solution) were also examined. FIG. 8B shows results of hybridizations between MBs free in solution and their target sequences. Conditions and experimental procedures were the same as those in FIG. 8A. The DNA1' solution contained 0.6 μM DNA1' and 0.1 μM MB (curve 1), and the DNA2' solution contained 0.6 μM DNA2' and 0.1 μM MB (curve 2). Curve 3 shows control with MB only in solution. Comparing results in FIGS. 8A and 8B, a marked difference was seen between the melting profiles of duplexes formed by MB immobilized on GMNC surfaces (FIG. 8A) and those in solution (FIG. 8B). It was clear that the melting temperature profiles for MB duplexes with both DNA1' and DNA2' were shifted to a higher temperature when the MBs were immobilized on GMNC surfaces. This point is further illustrated in FIG. 8C, which shows a direct comparison of the melting profiles of the duplexes formed between MB and DNA2' under the two conditions, i.e., MB immobilized on the GMNC surface (curve 1), and MB in buffer solution (curve 2). As shown in FIG. 8C, the temperature at which the DNA2'-MB duplex began to dissociate was shifted from 10<C for MB in solution to 18<C for MB bound to GMNC.

(E) Use of MB-GMNCs for Retrieval of Trace Amounts of Target DNAs from a Complex DNA-Protein Mixture.

To further probe the capabilities of MB-GMNCs, the efficiency of recovery of trace amounts of target DNAs from a complex protein/polynucleotide mixture was investigated. Three different general proteins, Hb, BSA, Lyz, and two 15-base random oligonucleotides (DNA3' and DNA4') were analyzed for their the ability to interfere with capability of the MB-GMNCs to bind to their target DNAs (i.e., DNA1' and DNA2'). A solution (9.90 ml volume) was prepared containing $10^{-7}$ M each of Hb, BSA, Lyz, $10^{-8}$ M each of DNA3' and DNA4', and 3 fmol ($3.13 \times 10^{-10}$M) each of DNA1' and DNA2', to which a 0.1 ml aliquot of a MB-GMNC-containing solution was added. The separation was carried out according to the steps described above.

Figure 9:
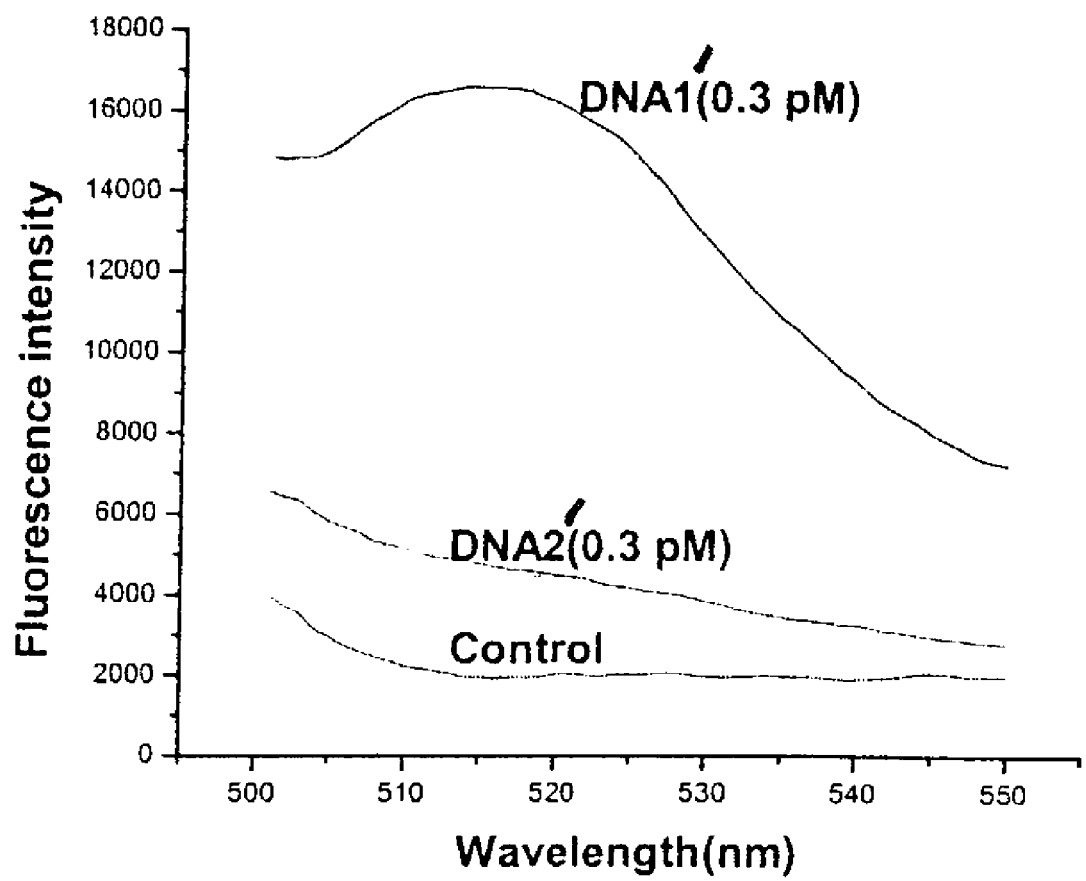
FIG. 9 is a graph showing the ability of MB-GMNCs to capture trace amounts of DNA targets from a complex DNA-protein mixture.

DNA1' and DNA2' specifically hybridized with the MB on the GMNC surfaces while the random DNA sequences and proteins did not. Following magnetic separation of the MB-GMCs, the fluorescence signals of DNA1' and DNA2' were measured. As seen in FIG. 9, the MB-GMNCs were able to capture trace amounts, i.e., 3 fmol, of the targets, DNA1' and DNA2', from the complex mixture of oligonucleotides and proteins. In these studies, complementary DNA1' was collected at concentrations as low as $3 \times 10^{-15}$ M, while the one-base mismatched DNA2' was collected at concentrations as low as about $9 \times 10^{-15}$ M. The study was performed in this instance using only a conventional spectrometer. Using more sensitive analytical methods (see, e.g., Fang and Tan, Anal. Chem. 71, 3101-3105, 1999; Zhang and Tan, Chem.-Eur. J. 6, 1087-1092, 2000), capture of even lower concentrations of targets should be detectable.

(F) Efficiency Rates for Capture of DNA Targets Using MB-GMNCs.

The efficiency of MB-GMNCs for the collection and separation of their complementary DNAs and those with single-base mismatches was further investigated using DNA1' and DNA2' in the complex DNA-protein mixture described above. In one set of tests, solutions of DNA1' and DNA2', both at concentrations of 25 nM, were hybridized with an excess of MB-GMNCs, and the fluorescence spectra of the two solutions were obtained by spectrometry. At the same time, a mixture of 25 nM DNA1' and 25 nM DNA2' was prepared and the DNA1' and DNA2' were separated from it according to the procedures and steps described above. After separation and collection of DNA1' and DNA2', an excess of MB-GMNCs, in the same concentration as used prior to separation, was added to the separated DNA1' and DNA2' solutions, respectively and the fluorescence was measured. No differences in the amounts of DNA1' or DNA2' before and after separation and collection were observed. Results showed that the efficiency of separation and collection was above 97% using DNA targets at a concentration of 25 nM ($2.5 \times 10^{-10}$M).

To determine the collection efficiency of the method at other target concentrations, complex samples with lower concentrations of DNA1' and DNA2' (i.e., in the picomolar range) were tested with the MB-GMNCs. Results, averaged from five experimental repeats under each condition, are summarized in Table 1. In each mixture, the concentrations of potential interferants were the same. Even at concentrations of target DNA1' and DNA2' as low as $8.25 \times 10^{-12}$M, the collection efficiency was close to or higher than 95%.

designed for DNA hybridization studies with the designer MBs and linear probes. All DNA sequences are shown in Table 2.

TABLE 2

Sequences of DNA Probe And Targets

| | |
|---|---|
| MB1 | 5'-ATC AAT ATT TAA CAA-3' (SEQ ID NO:7) |
| Target DNA1 (perfect complement to MB1 loop sequence) | 5'-TTG TTA AAT ATT GAT-3' (SEQ ID NO:8) |
| Target DNA2 (single base mismatch to MB1 loop sequence) | 5'-TTA TTA AAT ATT GAT-3' (SEQ ID NO:9) |
| Random DNA3 | 5'-TAG TFI7A TAA ATT GTT-3' (SEQ ID NO:10) |
| Random DNA4 | 5'-TAG TTA TAA ATT ATT-3' (SEQ ID NO:11) |
| MB2 | 5'-TMR(-C6Am)GCA CGT CCA TGC CCA GGA AGG AAC G (Bioton dT)GC(DABCYL)-3' (SEQ ID NO:12) |
| Target DNA5 (perfect complement to MB2 loop sequence) | 5'-TTC CTT CCT GGG CAT GGA-3' (SEQ ID NO:13) |
| bases 815-832 of 204 nt γ-actin mRNA (complementary to MB2 loop sequence) | TTC CTT CCT GGG CAT GGA (SEQ ID NO:14) |
| Linear DNA probe | 5'-Fluorescein1C ATC AAT ATT TAA CAA-3' (SEQ ID NO:15) |

TABLE 1

Efficiency of separation of DNA1' and DNA2' from a complex mixture*

| Sample No. | Target concentration in the the mixture (pM) | | Target concentration after separation (pM) | | Collection efficiency (%) | |
|---|---|---|---|---|---|---|
| | DNA1' | DNA2' | DNA1' | DNA2' | DNA1' | DNA2' |
| 1 | 25.0 | 25.0 | 24.4 | 24.3 | 97.6 | 97.2 |
| 2 | 12.5 | 50.0 | 11.8 | 48.5 | 94.4 | 96.9 |
| 3 | 8.25 | 8.25 | 7.82 | 8.15 | 94.8 | 98.8 |
| 4 | 8.25 | 100.0 | 8.56 | 98.6 | 103.4[#] | 98.6 |

*In each sample, the concentrations of Hb, BSA, Lyz were $1 \times 10^{-7}$ M, and the concentrations of DNA3 and DNA3 were $1 \times 10^{-8}$ M. Concentrations of target DNA1' and DNA2' ranged from 8.25-25 $\times 10^{-12}$ M and 8.25-100 $\times 10^{-12}$ M, respectively.
[#]error due to small volume measurement.

G. Use of MB-GMNCs for Capture Of mRNA from Mixtures

Synthesis of molecular beacons. A first molecular beacon (MB1; SEQ ID NO:7) was designed as described above with a 15-nucleotide loop and 5-nucleotide arms. Fluorescein was chosen as the fluorophore and DABCYL [4-(4'-dimethylaminophenylazo) benzoic acid] as the quencher. A second MB (MB2) was designed with a 18 base loop and 5 base arms. This loop sequence is complementary to part of a rat 204 nucleotide (nt) γ-actin mRNA. To compare linear DNA probes with molecular beacons, a 15 base linear DNA probe, with the same sequence as the loop sequence of MB1, was designed with fluorescein as the fluorophore. Targets to the linear DNA probe were labeled with DABCYL as the quencher. Several different target DNA sequences were TABLE 2-continued Sequences of DNA Probe And Targets

| | |
|---|---|
| Target DNA 6 (perfect complement to linear DNA probe) | 5'-TTG TTA AAT ATT GAT G/DABCYL-3' (SEQ ID NO:16) |
| Target DNA7 (single base mismatch to linear DNA probe) | 5'-TTA TTA AAT ATT GAT G/DABCYL-3' (SEQ ID NO:17) |

Preparation of γ-actin mRNA. RNA was isolated from rat lung tissues and then reverse transcribed to cDNA with oligo (dT) primer using a cDNA cycle kit (Introgen BV). The primer pair, 5'-GCG CTT CCG GTG TCC AGA-3' (SEQ ID NO:18) and 5'-GCC AGG GCT GTG ATC TCC-3'(SEQ ID NO:19), was used for PCR amplification. The reaction was run for 25 cycles. The PCR product of a 204-bp DNA fragment was cloned using the PCR2.1 vector (TA Cloning Kit, Invitrogen). The recombinant plasmid was then transformed into E. Coli INVα cells. Minipreps of the DNA prepared and linearized with BamHI. To produce γ-actin RNA, 1.0 μg of linearized plasmid DNA template was used in Ambion Megascript for the T7 transcription reaction. After purification, the 204 nt rat γ-actin mRNA was produced.

Capture of trace amounts of mRNA from a mixture. To determine the ability of MB-GMNCs to collect mRNA and PCR products from a mixture, artificial mixtures containing the 204-nt rat γ-actin mRNA fragments (bases 782-985, bases 815-832 complementary to the MB2 loop sequence) were prepared. Proteins and random DNA sequences in the mixture were the same as those described above in Example 5E.

DNA separation procedure. A calibration curve of fluorescence intensities for varying concentrations of mRNA was plotted using the pure MB2 and mRNA. After hybridization at room temperature, the fluorescence intensity of the MB increased in a similar manner to that for hybridization to MB2 with the perfectly complementary target DNA5. This result demonstrated that the MB was able to hybridize with the target mRNA even though the sequence of the target was over 10 times longer than the MB. Results of these experiments also showed that when the concentration of mRNA was very low, the hybridization time for the mRNA to its target was longer.

Following calibration, mixtures containing different concentrations of mRNA were added to the MB-GMNC solutions. For samples with low mRNA concentrations, a hybridization time of 60 min was used to ensure that all mRNA was detected. The MB-GMNCs were separated from the mixture using an applied magnetic field, following the separation procedures described above for the DNA separation studies. The collected mRNA amounts were investigated by detecting fluorescence intensities of the solutions after hybridizing the MB-GMNCs to the mRNA. The collection efficiencies of the MB-GMNC for mRNA are shown in Table 3.

TABLE 3

Efficiency of the separation of DNA1 and DNA2 from the mixture*

| Sample No. | Concentration before separation (pM) | | Concentration after separation (pM) | | Recovery (%) | |
|---|---|---|---|---|---|---|
| | DNA1 | DNA2 | DNA1 mean ± SD, n = 5 | DNA2 mean ± SD, n = 5 | DNA 1 (%) | DNA 2 (%) |
| 1 | 8.25 | 100.0 | 8.56 ± 0.28 | 98.6 ± 1.01 | 103.4# | 98.6 |
| 2 | 12.5 | 50.0 | 11.8 ± 0.74 | 48.5 ± 0.72 | 94.4 | 96.9 |
| 3 | 25.0 | 25.0 | 24.4 ± 0.45 | 24.3 ± 0.63 | 97.6 | 97.2 |
| 4 | 50.0 | 12.5 | 46.9 ± 0.71 | 11.1 ± 0.57 | 93.8 | 88.8 |
| 5 | 8.25 | 8.25 | 7.57 ± 0.52 | 8.15 ± 0.44 | 91.8 | 98.8 |
| 6 | mRNA: 10.0 pM | | 9.30 ± 0.73 | | 93.0 | |
| 7 | mRNA: 15.0 pM | | 14.7 ± 0.79 | | 98.7 | |
| 8 | mRNA: 20.0 pM | | 18.9 ± 0.47 | | 94.5 | |

*In each sample, the concentrations of Hb, BSA, Lyz are $1 \times 10^{-7}$ M; the concentrations of DNA3 and DNA3 are $1 \times 10^{-8}$ M.
May be due to errors in small volume measurements.

H. Use of MB-GMNCs for Capture of mRNA from Cells

MB-GMNCs were used to collect an mRNA sequence of 156 bases from cultured HTB-26 cells. A breast cancer cell line, HTB-26 (obtained from American Type Culture Collection) was cultured in 90-mm flasks according to the supplier's directions. Cell lysis was performed by adding extraction/BME buffer to the cells with continuous vortexing for 1 min. To clear the homogenate of cell debris and precipitate proteins, the lysate was centrifuged at 12,000×g for 10 minutes at room temperature. The supernatant containing mRNA was decanted and denatured at 70° C. for 5 min. MB-GMNCs were mixed with the cell lysate in dilution buffer with 1% β-mercaptoethanol. The MB-GMNCs were subsequently separated from the solution by subjecting the mixture to a magnetic field and fluorescence intensity was then detected directly. The 18 bases in the mRNA sequences were perfectly complementary to the MB2 loop sequence. There is no other mRNA molecule having the same 18 bases within HTB-26 cells.

Figure 10:
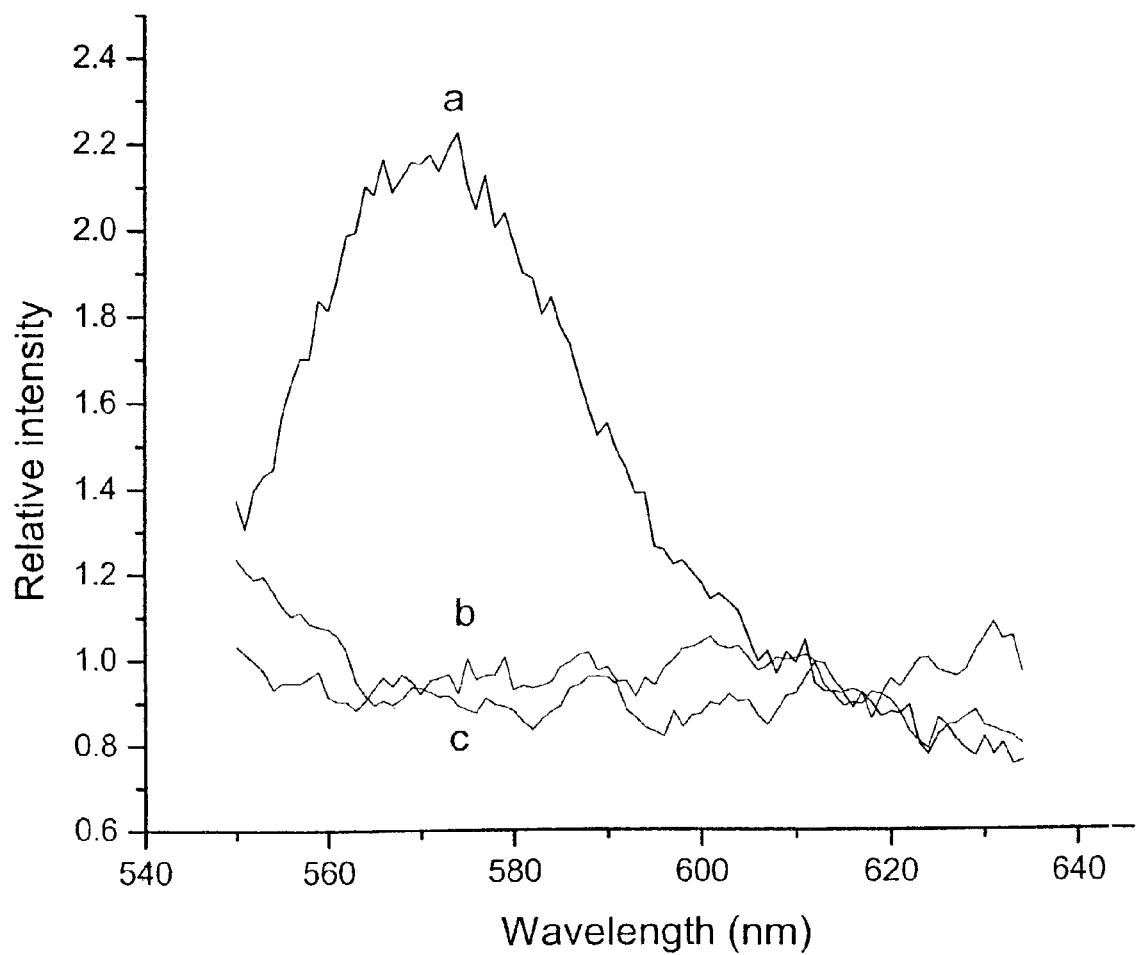
FIG. 10 is a graph showing the ability of MB-GNMCs to capture trace amounts of a target mRNA from a cell lysate.

Capture of mRNA from cultured cells. Following mRNA extraction from the cells, the mRNA molecules were specifically captured by the MB-GMNCs. This was evidenced by obvious fluorescent signals detectable in the MB-GMNCs separated from the cell lysates (FIG. 10, curve a). Results of two control experiments confirmed that the fluorescent signals were indeed due to the hybridization of the MB with the target mRNA. One control was performed by adding the MB-GNMCs before lysing the cells, followed by magnetic separation and washes. As shown in curve b, no fluorescence was detectable in the MB-GMNC solution when analyzed under the same conditions as in curve a. Additionally, when a MB with a different sequence from that of MB2 was incubatated with HTB-26 cell lysates under the same conditions, no detectable fluorescent signal was observed in the MB-GMNC solution (FIG. 10, curve c).

Example 6

Labeling of Bacteria

Dye-doped nanoparticles were conjugated with antibodies specific for E. coli strain O157:H7. These antibody-conjugated nanoparticles and unconjugated nanoparticles (as a negative control) were separately mixed with a solution containing E. coli strain O157:H7 for a time sufficient for the antibody to bind antigen. The mixture was then filtered and analyzed by scanning electron microscopy (SEM) and fluorescence microscopy. SEM and fluorescence microscopy both showed that the antibody-conjugated nanoparticles, but not the unconjugated nanoparticles, became associated with the bacteria.

Other Embodiments

While the above specification contains many specifics, these should not be construed as limitations on the scope of the invention, but rather as examples of preferred embodiments thereof. Many other variations are possible. Accordingly, the scope of the invention should be determined not by the embodiments illustrated, but by the appended claims and their legal equivalents.

What is claimed is:

1. A functionalized magnetic nanoparticle comprising a metal core and a silica surface, the silica surface being conjugated with at least one functional group comprising an oligonucleotide in the form of a molecular beacon, wherein the sequence of said oligonucleotide comprises a single-stranded loop structure comprising a nucleic acid sequence of interest, and a stem-forming arm structure on either side of the sequence of interest, the two stem-forming arm structures comprising bases complementary to one another that form a stem when hybridized with one another, said oligonucleotide further comprising a fluorophore attached at one end of said sequence, and a quencher attached at the other end of said sequence, wherein fluorescence emission of the fluorphore is inhibited by the quencher when the stem-forming structures are hybridized to one another in the absence of a complement of the nucleic acid sequence of interest.

2. The functionalized nanoparticle of claim 1, wherein the molecular beacon is conjugated to the silica surface by a biotin-avidin linkage.

3. The functionalized nanoparticle of claim 1, wherein the sequence of said oligonucleotide differs from the target sequence by one base.

4. A functionalized magnetic nanoparticle comprising a metal core and a silica surface, the silica surface being conjugated with at least one functional group comprising an oligonucleotide in the form of a molecular beacon, wherein the sequence of said oligonucleotide comprises a single-stranded loop structure comprising a nucleic acid sequence of interest and wherein the sequence of said oligonucleotide differs from the target sequence by one or more bases, and a stem-forming arm structure on either side of the sequence of interest, the two stem-forming arm structures comprising bases complementary to one another that form a stem when hybridized with one another, said oligonucleotide further comprising a fluorophore attached at one end of said sequence, and a quencher attached at the other end of said sequence, wherein fluorescence emission of the fluorphore is inhibited by the quencher when the stem-forming structures are hybridized to one another in the absence of a complement of the nucleic acid sequence of interest.

* * * * *

UNITED STATES PATENT AND TRADEMARK OFFICE
CERTIFICATE OF CORRECTION

PATENT NO. : 7,524,630 B2
APPLICATION NO. : 10/421491
DATED : April 28, 2009
INVENTOR(S) : Weihong Tan et al.

Page 1 of 1

It is certified that error appears in the above-identified patent and that said Letters Patent is hereby corrected as shown below:

Col. 1, line 20, please replace "may have certain rights" with "has certain rights".

Signed and Sealed this

Eighteenth Day of August, 2009

David J. Kappos
*Director of the United States Patent and Trademark Office*